(12) United States Patent
Pawar et al.

(10) Patent No.: US 11,596,720 B2
(45) Date of Patent: *Mar. 7, 2023

(54) BIOFILM RESISTANT MEDICAL IMPLANT

(71) Applicant: Smith & Nephew, Inc., Memphis, TN (US)

(72) Inventors: Vivek D. Pawar, Germantown, TN (US); John Rose, Collierville, TN (US); Carolyn Weaver, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 726 days.

This patent is subject to a terminal disclaimer.

(21) Appl. No.: 16/545,993

(22) Filed: Aug. 20, 2019

(65) Prior Publication Data

US 2020/0000977 A1  Jan. 2, 2020

Related U.S. Application Data

(63) Continuation of application No. 14/905,168, filed as application No. PCT/US2014/048219 on Jul. 25, 2014, now Pat. No. 10,413,640.

(Continued)

(51) Int. Cl.
*C23C 8/10* (2006.01)
*A61L 31/16* (2006.01)
(Continued)

(52) U.S. Cl.
CPC .............. *A61L 31/16* (2013.01); *A61L 27/04* (2013.01); *A61L 27/047* (2013.01); *A61L 27/06* (2013.01);
(Continued)

(58) Field of Classification Search
CPC ............... C23C 18/38; A61L 2300/104; A61L 2300/404; A61L 2300/606
See application file for complete search history.

(56) References Cited

U.S. PATENT DOCUMENTS 7,771,774 B2   8/2010  Berckmans, III et al.
8,945,363 B2 * 2/2015  Pickford ............... A61L 27/306
                                                              205/85

(Continued)

FOREIGN PATENT DOCUMENTS

EP       0926256 B1     5/2003
EP       1494729 B1    11/2005
(Continued)

OTHER PUBLICATIONS

Decision of Rejection for JP Patent Application No. 2016-530075 dated Mar. 11, 2019.
(Continued)

*Primary Examiner* — Lois L Zheng
(74) *Attorney, Agent, or Firm* — KDB Firm PLLC

(57) ABSTRACT

A method of incorporating silver and/or copper into a biomedical implant includes: providing an implant having an outer surface; depositing silver and/or copper onto the outer surface of the implant; diffusing the silver and/or copper into a subsurface zone adjacent the outer surface; and oxidizing or anodizing the implant after the diffusion step to form an oxidized or anodized layer that contains at least some amount of elemental silver, elemental copper or silver or copper ions or compounds.

19 Claims, 15 Drawing Sheets

Related U.S. Application Data

(60) Provisional application No. 61/858,953, filed on Jul. 26, 2013.

(51) Int. Cl.

| | | |
|---|---|---|
| *A61L 27/54* | (2006.01) | |
| *A61L 31/02* | (2006.01) | |
| *A61L 31/14* | (2006.01) | |
| *A61L 27/04* | (2006.01) | |
| *A61L 27/50* | (2006.01) | |
| *A61L 27/06* | (2006.01) | |
| *A61L 27/30* | (2006.01) | |
| *A61L 31/08* | (2006.01) | |
| *C22F 1/18* | (2006.01) | |
| *C23C 14/02* | (2006.01) | |
| *C23C 14/16* | (2006.01) | |
| *C23C 14/24* | (2006.01) | |
| *C23F 17/00* | (2006.01) | |
| *C23C 8/00* | (2006.01) | |

(52) U.S. Cl.
CPC .............. *A61L 27/30* (2013.01); *A61L 27/50* (2013.01); *A61L 27/54* (2013.01); *A61L 31/022* (2013.01); *A61L 31/088* (2013.01); *A61L 31/14* (2013.01); *C22F 1/183* (2013.01); *C23C 14/028* (2013.01); *C23C 14/16* (2013.01); *C23C 14/24* (2013.01); *C23F 17/00* (2013.01); *A61L 2300/104* (2013.01); *A61L 2300/404* (2013.01); *A61L 2300/606* (2013.01); *A61L 2400/18* (2013.01); *A61L 2430/02* (2013.01)

(56) References Cited

U.S. PATENT DOCUMENTS

| | | |
|---|---|---|
| 2007/0298377 A1 | 12/2007 | Kenealy et al. |
| 2008/0195222 A1 | 8/2008 | Rauguth et al. |
| 2010/0326835 A1 | 12/2010 | Speitling |

FOREIGN PATENT DOCUMENTS

| | | |
|---|---|---|
| EP | 1958650 A1 | 8/2008 |
| JP | 2005523079 A | 8/2005 |
| JP | 2008194463 A | 8/2008 |
| JP | 2010515513 A | 5/2010 |
| JP | 2010540779 A | 12/2010 |
| WO | 2003089023 A1 | 10/2003 |
| WO | 2007066669 A1 | 6/2007 |
| WO | 2008087448 A1 | 7/2008 |

OTHER PUBLICATIONS

Japanese Office Action; Japanese Patent Office; Japanese Application No. 2016-530075; dated May 21, 2018; 11 pages.
Australian Examination Report No. ; Australian Patent Office; Australian Application No. 2014292972; dated May 5, 2017; 2 pages.
International Search Report; Korean Intellectual Property Office; International Patent Application No. PCT/US2014/048219; dated Nov. 5, 2014; 3 pages.
Written Opinion of the International Searching Authority; Korean Intellectual Property Office; International Patent Application No. PCT/Us2014/048219; dated Nov. 5, 2014; 8 pages.
European Examination Report; European Patent Office; European Application No. 14830097.3; dated Mar. 2, 2017; 8 pages.
Ming Wen et al.; "Synthesis and characterization of nanostructured Ag on porous titania", Applied Surface Science, Elsevier, Amsterdam, NL, vol. 257, No. 11, Dec. 18, 2010 (Dec. 18, 2010), pp. 4836-4843, KP028142196, ISSN: 0169-4332, DOI: 10.1016/J.APSUSC.2010.12.102 [retrieved on Dec. 24, 2010].
V. Stranak et al.; "Depostion of thin titanium copper films with antimicrobial effect by advanced magnetron sputtering methods", Materials Science and Engineering C, Elsevier Science S.A, CH, vol. 31, No. 7, Jun. 20, 2011 (Jun. 20, 2011), pp. 1512-1519, XP028272960, ISSN: 0928-4931, DOI: 10.1016/J.MSEC.2011.06 009 [retrieved an Jun. 25, 2011].
Edin Zhang et al.; "A new antibacterial titanium-copper sintered alloy: Preparation and antibacterial property", Materials Science and Engineering C, vol. 33, No. 7, pp. 4280-4287, XP028686244, ISSN: 0928-4931, DOI: 10.1016/J.MSEC.2013.06.016.

\* cited by examiner

BIOFILM RESISTANT MEDICAL IMPLANT

CROSS-REFERENCE TO RELATED APPLICATION

This application is a continuation of pending U.S. patent application Ser. No. 14/905,168, filed Jan. 14, 2016, which is a U.S. National Phase of International PCT Application No. PCT/US2014/048219, filed on Jul. 25, 2014, which claims the benefit of U.S. Provisional Application No. 61/858,953 filed Jul. 26, 2013, the contents of each application incorporated herein by reference in their entirety.

BACKGROUND

Orthopedic fixation devices may be used, for example, to stabilize an injury, to support a bone fracture, to fuse a joint, and/or to correct a deformity. An orthopedic fixation device may be attached permanently or temporarily, and may be attached to the bone at various locations, including implanted within a canal or other cavity of the bone, implanted beneath soft tissue and attached to an exterior surface of the bone, or disposed externally and attached by fasteners such as screws, pins, and/or wires. Some orthopedic fixation devices allow the position and/or orientation of two or more bone pieces, or two or more bones, to be adjusted relative to one another. Orthopedic fixation devices are generally machined or molded from isotropic materials, such as metals including, for example, titanium, titanium alloys, stainless steel, cobalt-chromium alloys, and tantalum.

Treatment of fractures that require open reduction and fixation usually heal normally without issues. In some cases, however, this normal healing response is impaired due to the presence of an infection. Once an infection is present, it is believed that a biofilm can form on an implant within 24 hours. Once formed, the biofilm provides an environment that protects microbes from antibiotics, thereby making eradication of the infection much more difficult. Further, the formation of a biofilm can result in later infections. If repeat infections are an issue before a fracture heals, then an exchange of the hardware may be required. If infections occur after the fracture has healed, then the hardware must be removed. Once the hardware with a suspected biofilm is removed, the infection issues usually resolve. An implant that resists biofilm formation has the potential to substantially reduce the incidence of hardware-related infections and also to substantially reduce the number of additional operations required in infected patients. Thus, there remains a need for further development of biofilm resistant implants and methods of producing the same. The present invention addresses this need and provides other benefits and advantages in a novel and unobvious manner.

SUMMARY OF THE DISCLOSURE

The various embodiments of the present invention described herein and shown in the Figures provide devices that resists biofilm formation. This is achieved by making a device that locally releases an antimicrobial element into the body fluid adjacent to the implant, which kills or significantly reduces any microbes around the implant before they have a chance to colonize the implant. While the actual nature of the invention covered herein can only be determined with reference to the claims appended hereto, certain forms and features of the invention that are characteristic of the embodiments disclosed herein are described briefly as follows.

In one aspect, the present disclosure provides a method for imparting biofilm resistance to an implant device, the implant device being wholly or partially composed of a metallic substrate, the method including: (i) depositing silver, copper or both silver and copper onto a surface of the metallic substrate; (ii) diffusing the silver, copper or both silver and copper into a subsurface zone of the substrate, the subsurface zone being adjacent the surface and extending to a depth below the surface; and (iii) oxidizing or anodizing the substrate, thereby forming an oxidized or anodized layer at the surface of the substrate. In one embodiment, the method further includes modifying the surface of the substrate to increase the surface area of the substrate before the silver, copper or both silver and copper is deposited onto the surface. The surface can be modified by a physical roughening treatment, by a chemical treatment that includes soaking the substrate in an alkaline solution for a period of time of about 1 hour to about 24 hours, or by both a physical roughening treatment and the chemical treatment. With regard to the chemical treatment, in one embodiment the soaking is performed at a temperature of from about 30 to about 90° C. In another embodiment, the alkaline solution comprises sodium hydroxide.

In another aspect, the disclosure provides a method of incorporating silver, copper or both silver and copper into a metallic biomedical implant, the method including: (i) providing an implant comprising a biomedical metal or a biomedical alloy having an outer surface; (ii) depositing silver, copper or both silver and copper onto the outer surface; (iii) diffusing silver, copper or both silver and copper into the biomedical metal or biomedical alloy beneath the outer surface; and (iv) oxidizing or anodizing the outer surface after said diffusing to form an oxidized or anodized layer. In one embodiment, the method further includes roughening the outer surface before the silver, copper or both silver and copper is deposited onto the surface.

Further areas of applicability of the invention will become apparent from the detailed description provided hereinafter. It should be understood that the detailed description and specific examples, while indicating certain embodiments of the invention, are intended for purposes of illustration only and are not intended to limit the scope of the invention.

BRIEF DESCRIPTION OF THE DRAWINGS

The accompanying drawings, which are incorporated in and form a part of the specification, illustrate embodiments of the invention and together with the written description serve to explain the principles, characteristics, and features of the invention. In the drawings.

DETAILED DESCRIPTION

For the purpose of promoting an understanding of the principles of the present invention, reference will now be made to representative embodiments and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates. The following descriptions and illustrations of non-limiting forms and embodiments of the present invention are exemplary in nature, it being understood that the descriptions and illustrations related thereto are in no way intended to limit the inventions disclosed herein and/or their applications and uses.

An implant device having enhanced resistance to biofilm formation is made by incorporating silver and/or copper into the device in a manner whereby the silver and/or copper is releasable into the surrounding tissues and/or fluids at a desirable rate over an extended period of time following implantation of the device. For purposes of describing various embodiments, the term "metallic substrate" refers to, among other things, the metallic material of which an implant device or component of an implant device is made and into which silver and/or copper is incorporated as described herein.

A method for incorporating a biocidal amount of silver and/or copper into a metallic substrate, such as a biomedical metal or biomedical alloy, includes depositing silver and/or copper onto a surface of the substrate; diffusing the silver and/or copper into a subsurface zone of the substrate adjacent the surface, referred to herein as a "diffusion zone", the diffusion zone extending to a depth below the surface that is dependent, at least in part, on the diffusing conditions; and oxidizing or anodizing the substrate, thereby forming an oxidized or anodized layer at the surface of the substrate. In one embodiment, the oxidized or anodized layer contains at least some amount of silver and/or copper, such as, for example, in the form of elemental silver, elemental copper or silver or copper ions or compounds. In some embodiments, some quantity of silver and/or copper also remains on the surface of the metallic substrate following the diffusing and the oxidizing or anodizing. In some embodiments described further herein, methods further include a modification of the substrate's surface prior to deposition of silver and/or copper thereon.

Figure 1:
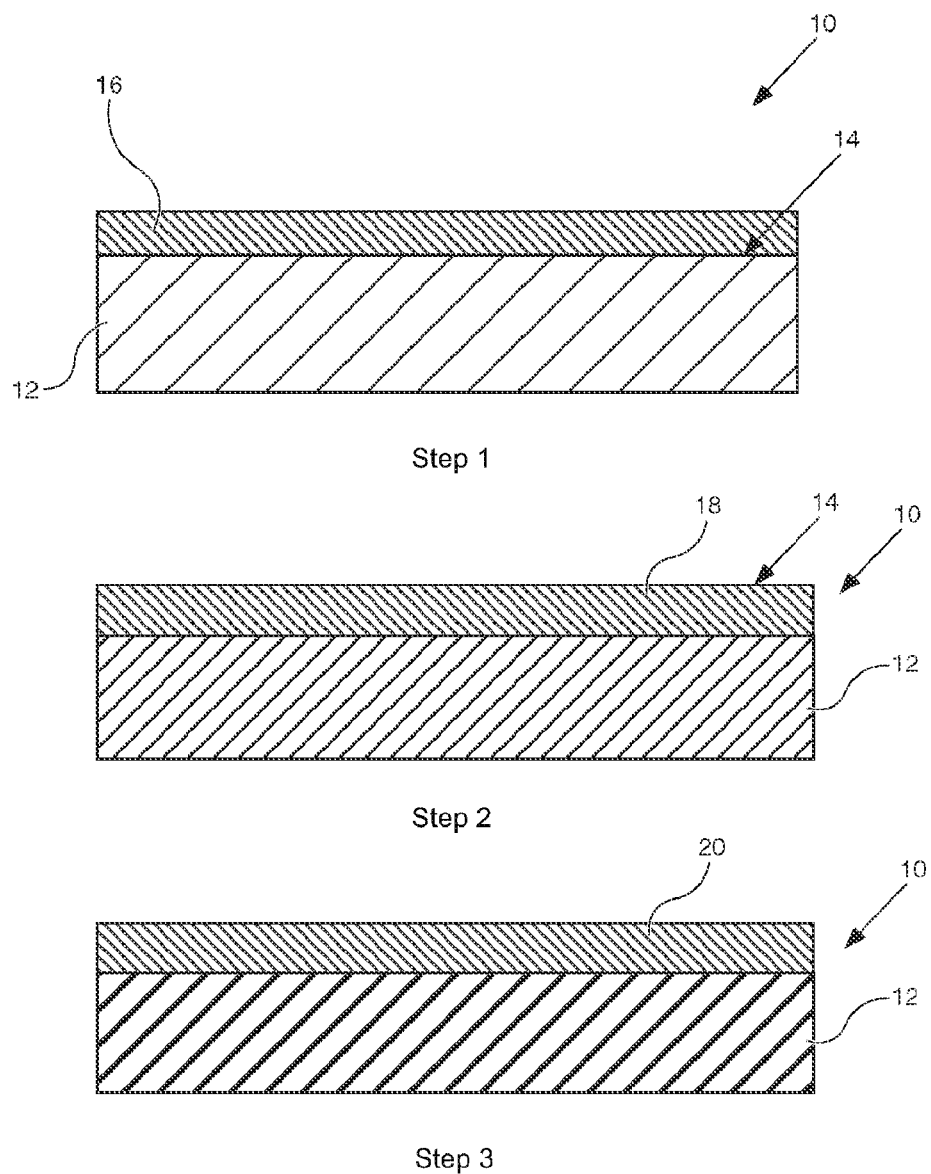
FIG. 1 shows a schematic of a disclosed method.

FIG. 1 is a schematic representation of one embodiment of the disclosed method.

FIG. 1 depicts an implant 10. The implant 10 has a substrate 12 and a surface 14. In step 1, optionally after the surface is roughened, a layer 16 is deposited on the surface 14. In the depicted embodiment the layer 16 is made of silver, however, in other embodiments the layer 16 is made of copper or of a mixture of silver and copper. In step 2, the layer 16 is diffused into the substrate 12 to a depth below the surface 14 and with a certain diffusion profile to form a diffusion layer 18 (also referred to herein as "diffusion zone" and "subsurface zone"). In step 3, the surface and the diffusion layer 18 (partially or completely) is oxidized or anodized to form an oxidized or anodized layer 20 that contains at least some amount of elemental silver, silver oxide or silver compounds. It should be noted that based on the cross-section depictions of FIG. 1, it appears that there is a distinct boundary between the substrate 12 and the subsurface zone 18 in step 2; however, those having ordinary skill in the art would understand that such a distinct boundary does not exist as some portion of silver will be alloyed to at least trace levels at an interface between diffusion zone 18 and substrate 12. The silver and/or copper concentration gradually changes from the surface 14 to the substrate 12, even though metallographically it is not visible.

Figure 2:
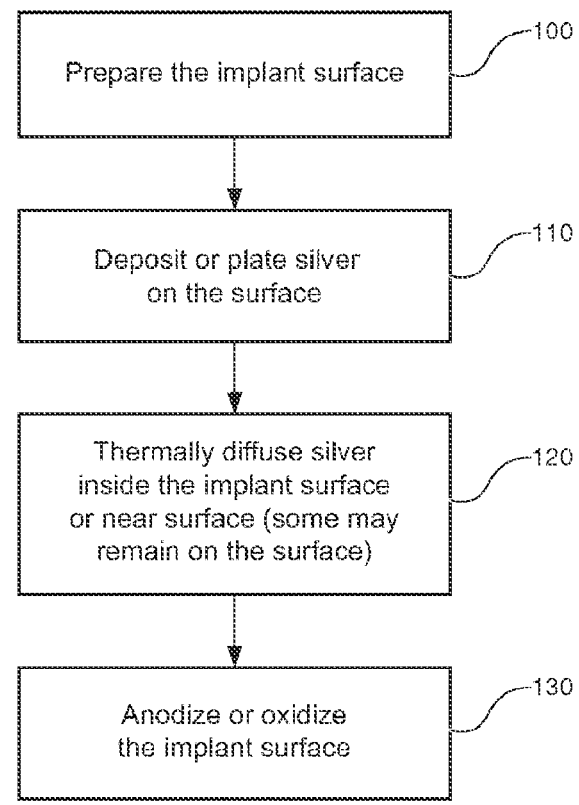
FIG. 2 shows a flow chart showing key steps of a disclosed method.

FIG. 2 depicts a flow chart showing key steps of one method embodiment. In step 100, the implant surface is prepared. In step 110, silver is deposited or plated onto the surface. In step 120, the silver is diffused into the subsurface zone of the implant. In some embodiments, some of the silver is diffused into the implant but some silver still remains on the surface. In step 130, the diffusion layer is anodized or oxidized. In alternative embodiments, one or more of steps 100, 110 and 120 can be repeated prior to the performance of step 130.

The term "biomedical metal or biomedical alloy" as used herein is intended to refer to individual metals or metal combinations (alloys) that are currently used in orthopedic industry. In one embodiment, the biocompatible metal comprises a transition metal, a transition metal alloy or a transition metal oxide. Examples of biocompatible alloys include cobalt-chromium-molybdenum, titanium-aluminum-vanadium, nickel-titanium and zirconium-niobium. Additional biocompatible alloys are made from either zirconium or titanium or tantalum or niobium or hafnium or combinations thereof. For example, the biocompatible metal can be titanium, a titanium alloy or titanium oxide. Titanium and its alloys, due to their high toughness and excellent biocompatibility are ideally suited as orthopedic implants. Optionally, the metallic substrate may comprise cobalt chrome, polished zirconium, OXINIUM® (Smith & Nephew, Inc.), oxidized zirconium or zirconium oxide, stainless steel, tantalum or any combination of these. The substrate may comprise any metal, or metal alloy, or metal oxide or combination of these but suitably it would comprise titanium or zirconium. In one embodiment, the biocompatible metal is pure titanium or pure zirconium with any additional metals less than 1% by weight.

In one embodiment, the substrate comprises a stainless steel, a titanium alloy, or a cobalt/chromium alloy. One suitable titanium alloy, for example, includes titanium, aluminum and niobium (referred to herein as "TiAlNb"). Another suitable titanium alloy, for example, includes 90% titanium with 6% aluminum and 4% vanadium (referred to herein as "Ti6Al4V"). An example of a suitable cobalt/chromium alloy includes 26.5-30% chromium and 4.5-7% molybdenum, with the remainder being cobalt. An example of a suitable zirconium alloy includes 97.2-97.6% zirconium and 2.4-2.8% niobium (referred to herein as "Zr-2.5Nb").

The substrate may be formed into an orthopedic implant or other medical implant device, either before or after the incorporation of silver or copper as described herein. The surface of the substrate into which silver or copper is incorporated as described herein can be the entire surface of the substrate, e.g., the entire surface of an implant that is composed of a biomedical metal or biomedical alloy, or only a portion of substrate's surface. Unless indicated otherwise, in this disclosure the terms "silver" and "copper" are intended to refer to these metals in their elemental state, in an ionic form, as a compound or in any other form.

Silver and/or copper can be deposited onto the surface of the metallic substrate using a variety of techniques known in the art, including, for example, physical gas phase deposition (also known as "physical vapor deposition" or "PVD"), chemical vapor deposition (also known as "CVD"), electrochemical plating, chemical dip, ion implantation, spraying or painting, to name a few.

In one embodiment, the silver and/or copper is deposited on the metallic substrate by physical vapor deposition. The term physical vapor deposition designates a group of vacuum-based coating methods in which the layer is formed directly by condensation of a material vapor of the starting material. The material which is to be deposited, which is designated as the target, is generally present in solid form in the generally evacuated coating chamber and is vaporized by bombardment with laser beams, magnetically deflected ions or electrons and by arc discharge. The extent of the proportion of atoms, ions or larger clusters in the vapor is different from method to method. The vaporized material moves either ballistically or is guided through electric fields through the chamber and in so doing impinges onto the parts of the metallic substrate that are to be coated, where the layer formation occurs. If all surfaces of the metallic substrate are to be coated as homogeneously as possible, the substrate typically must be moved in a suitable manner during coating, which can be achieved, for example, by rotation of the substrate. When the vapor particles impinge onto the substrate, they begin to deposit themselves on the surface by condensation. A PVD coating process can be carried out in commercially available PVD systems. In various embodiments of the method, a PVD covering layer of, for example, from about 5 micrograms/cm$^2$ to about 150 micrograms/cm$^2$ consisting of silver and/or copper is applied onto the surface of the metallic substrate.

In another embodiment, silver and/or copper is deposited on a metallic substrate using electrochemical plating process. The silver or copper plating solution can consist of organic or inorganic silver or copper compounds. The solutions can be used at room temperature or can be heated to a temperature of, for example, from about 50 to about 70° Celsius. In one embodiment a silver electrode is used as an anode and the implant or other metallic substrate to be coated is used as cathode. An external voltage applied dissociates silver ions in the solution, which in turn are deposited on the implant surface. In another embodiment the process is carried out using a platinum anode and with a solution containing silver ions (such as, for example, silver nitrate). In another embodiment, electro-less baths are used to create a thin silver layer on the implants. In this type of process, the implant is immersed in a silver nitrate bath, and then the implant optionally can be dipped in a reducing solution such as potassium sodium tartrate to reduce silver oxide (ions) formed on the surface to metallic silver.

As indicated above, either silver alone, copper alone or a combination of silver and copper can be deposited on the metallic substrate. In one embodiment, silver is deposited on the surface of the substrate. In another embodiment, copper is deposited on the surface. In yet another embodiment, both copper and silver are deposited on the surface. In an embodiment in which both silver and copper are deposited, the silver and copper can be deposited in any desired proportions. In one embodiment, the deposited material comprises from about 10 to about 60% silver by weight. In another embodiment, the deposited material comprises from about 80 to about 99% silver by weight. In another embodiment, the proportions of silver and copper in a deposited material is any proportion that does not form a eutectic composition.

In other embodiments, the method for making a biofilm resistant implant includes, before depositing silver and/or copper onto the surface of the metallic substrate as discussed above, modifying a surface of the substrate to provide a modified surface having an increased surface area relative to the substrate's surface area prior to the modification. In one embodiment, the increased surface area is achieved by a physical roughening treatment. In one embodiment, the surface has a roughness of from about 0.1 micron to about 10 micron Ra prior to deposition of silver and/or copper thereon.

Surface modification can be achieved, for example, by way of a grit roughening treatment, such as a sand blasting or a grit blasting treatment. Grit blasting is particularly useful for increasing the surface area of a metallic substrate that is composed of titanium or a titanium alloy. In one embodiment, the target surface can be modified by grit blasting the surface with abrasive particles such as alumina. In another embodiment, the modification of the surface can be achieved by way of grit paper roughening, which is particularly useful for increasing the surface are of a metallic substrate that is composed of zirconium or a zirconium alloy.

In another manner of increasing the surface area of a metallic substrate, the surface can be modified by a macro or micro physical surface-treatment in which a coating of metallic beads is adhered to the surface. The beads form a 3D porous geometry on the surface thereby providing a modified surface having a greater surface area than the unmodified surface. In one embodiment the modified surface comprises a double or triple layer of beads sintered onto the metallic substrate. In one embodiment in which the metallic substrate is composed of titanium or a titanium alloy, the beads are titanium beads. In another embodiment, the titanium beads have a mean diameter of from about 100 μm to about 500 μm. In yet another embodiment, the titanium beads have a mean diameter of about 328 μm. In another embodiment, in place of the beads, particles of an aspherical metal powder, for example particles composed of titanium, are adhered to the surface. In another embodiment, the longest dimension of the aspherical powder particles averages from about 50 μm to about 250 μm.

In another embodiment, the surface of the metallic substrate is modified by applying a coating thereto that contains a sponge- or foam-like network of metallic fibers and/or wires. In one embodiment, the foam or sponge-like structure is composed of sintered beads having diameters of between 15 and 50 μm and features pore diameters of several hundred microns to approximately 1 mm. Further information regarding surface treatments of this type is disclosed in commonly owned U.S. Publication No. 2011/0059312, the disclosure of which is incorporated herein by reference in its entirety.

Subsequent to the physical treatments discussed above, the modified surface of the metallic substrate can be chemically treated to further increase the surface area of the substrate. In one embodiment, the chemical treatment can be employed after one or more of the above-discussed physical treatments (e.g., after a grit roughening treatment, after adhering a coating of metallic beads on the surface or after forming a sponge- or foam-like coating on the substrate). In another embodiment, the chemical treatment is employed to create a nanotextured surface on the implant without a prior physical treatment. For titanium or titanium alloys this may be done by forming a titanate layer on the surface, as discussed further below.

In embodiments in which the metallic substrate is titanium or a titanium alloy, the chemical treatment can include, for example, soaking the substrate in an alkaline solution at approximately 30-90° C. In one embodiment, the temperature of the alkaline solution is between about 50 and 70° C. In another embodiment, the temperature of the alkaline solution is between about 55 and 65° C. The titanium or titanium alloy reacts with the alkaline solution to form alkali titanates, thus producing a modified surface that comprises alkali titanates, and typically also includes titanium oxide or titanium oxides. In one embodiment, the substrate is soaked in the alkaline solution for between 1 and 24 hours. In another embodiment, the soaking time is between 1 and 5 hours, and in yet another embodiment is between 1 and 3 hours.

The alkali titanate produced by soaking the substrate in an alkaline solution creates a modified surface that comprises a nanostructure of alkali titanates. A nanostructure or nanotextured surface generally means a surface that includes particles or elements of a size falling within the nanometer range. The nanostructure of alkali titanates resembles a strut-like morphology containing discrete elements, structurally resembling fibers or fibrils, of alkali titanate having a width of between 1 and 20 nanometers (nm). The fibrils are generally cylindrical in shape, typically have lengths ranging from about 200 to about 300 nm and the distance between fibrils typically ranges from about 5 nm to about 80 nm. The fibrils are generally overlaid or stacked one atop another forming the alkali titanate layer over the substrate. In one embodiment, the thickness of the alkali titanate layer is in the range of 100-500 nanometers. In another embodiment, the thickness of the alkali titanate layer is from about 100 to about 300 nanometers.

While physical treatments such as those described above themselves increase the surface area of the substrate, the formation of the alkali titanate nanostructure significantly further increases the surface area of the substrate and hence enables a significantly enhanced area of contact between the metallic substrate and the silver or copper deposited thereon in a subsequent deposition step.

In one embodiment, the alkaline solution comprises a hydroxide, a preferred hydroxide for this use being sodium hydroxide. Other hydroxides that can be used include lithium hydroxide, potassium hydroxide or any other suitable metal hydroxide. When sodium hydroxide is used, the alkali titanate nanostructure formed on the surface of the metallic substrate will be sodium titanate. Sodium titanate is an ionic compound that can be readily modified by ion-exchange chemistry into other compounds such as lithium titanate or strontium titanate to confer different physico-chemical or biocompatibility characteristics suitable for different applications. In one embodiment, the concentration of the hydroxide solution is between 2 and 8 molar. In another embodiment, the concentration of the hydroxide solution is between 3 and 6 molar. In yet another embodiment, the concentration is 4 molar. In one embodiment, the metallic substrate is soaked in a 4 molar solution of sodium hydroxide at 60° C. for two hours.

In another embodiment, the modification of the metallic substrate surface to increase surface area is achieved by an etching treatment. For example, the target surface can be etched using fluoride solutions (e.g., hydrofluoric acid and nitric acid solution or an ammonium fluoride solution) to remove the native oxide formed on the surface and to increase the surface area of the substrate prior to deposition of silver and/or copper.

After the silver and/or copper is deposited on the substrate, it is diffused into the subsurface zone of the substrate by a diffusion treatment. The diffusion is achieved by heating the implant, which can be performed in air or in a vacuum, for a period of time and at a temperature selected to dissolve the silver and/or the copper on the surface, and diffuse it into the substrate in the subsurface zone. In another embodiment, thermal diffusion is carried out in an inert atmosphere containing argon or helium or nitrogen. During the diffusion treatment, the silver and/or copper becomes integral with the metal of the substrate in the subsurface zone.

Figure 8:
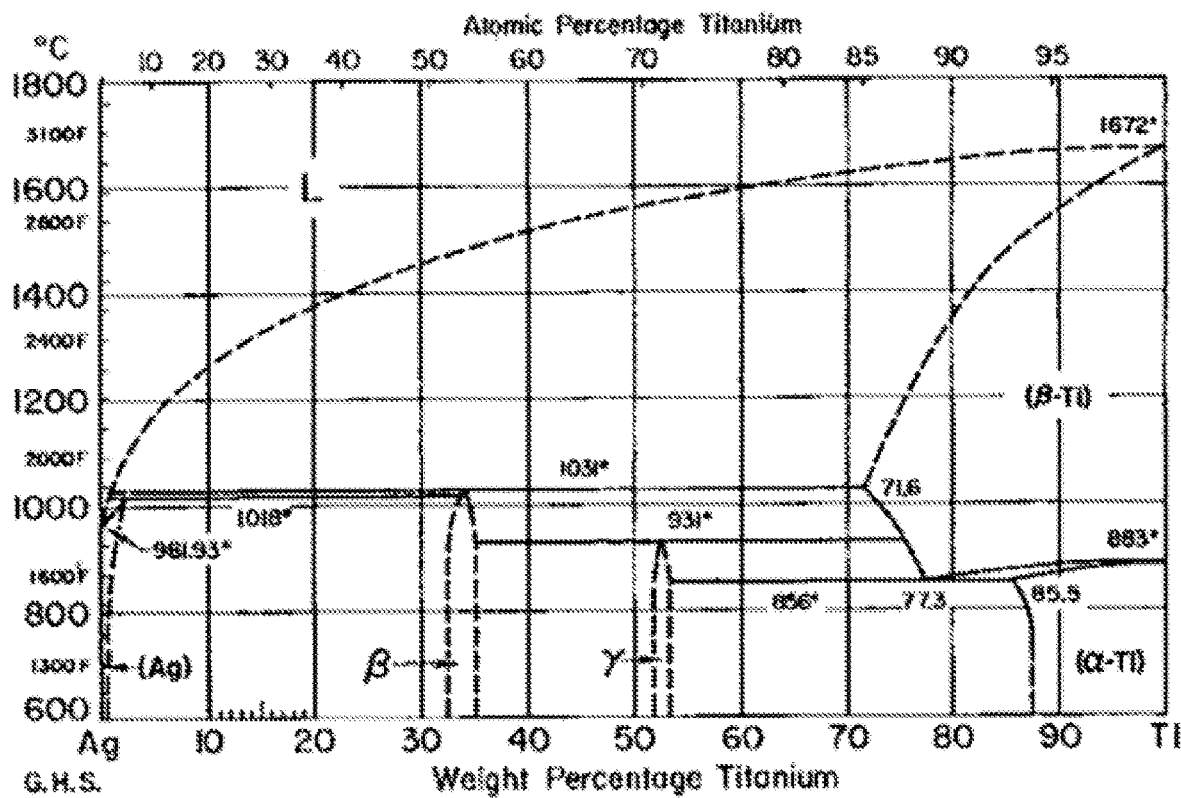
FIG. 8 is a phase diagram of a binary alloy system including silver and titanium. (8 American Society for Metals, Metals Handbook: Metallography, Structures and Phase Diagrams 256 ($8^{th}$ ed. 1973)).
Figure 9:
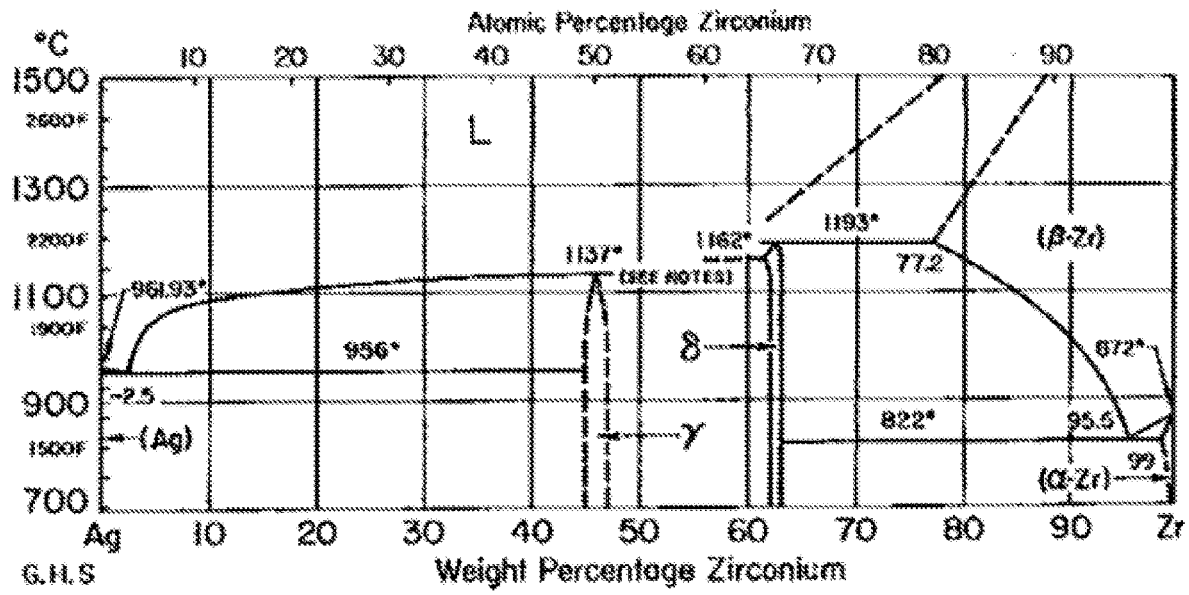
FIG. 9 is a phase diagram of a binary alloy system including silver and zirconium. (8 American Society for Metals, Metals Handbook: Metallography, Structures and Phase Diagrams 256 (8th ed. 1973)).

The temperature at which the diffusion is performed can be selected with the aid of a phase diagram to take advantage of the solubility characteristics of the silver and/or copper in the metal or metals primarily present in the substrate. For example, in an embodiment in which silver is diffused into a substrate composed primarily of titanium, such as, for example, a substrate composed of Ti6Al4V alloy, reference can be made to a silver-titanium phase diagram such as that set forth in FIG. 8. Similarly, in an embodiment in which silver is diffused into a substrate composed primarily of zirconium, such as, for example, a substrate composed of Zr-2.5Nb alloy, reference can be made to a silver-zirconium phase diagram such as that set forth in FIG. 9.

In one exemplary method, a Ti6Al4V substrate having commercially pure silver deposited thereon by PVD is heated to about 750° C. in vacuum, which may be, for example, less than about $10^{-4}$ torr. The silver-coated substrate is maintained at this temperature for a period of time sufficient for all or nearly all of the silver to become dissolved and diffused into the substrate in the subsurface zone, thereby resulting in a modification of the composition of the alloy in the subsurface zone of the substrate. In one embodiment, the amount of time required for completion of a desired degree of diffusion is dependent upon the amount of silver deposited on the surface and the surface area of the substrate prior to silver deposition. In one embodiment, the period of time is from about 15 minutes to about 10 hours. In another embodiment, the period of time is from about 30 minutes to about 2 hours. In yet another embodiment, the period of time is from about 15 minutes to about 45 minutes. After the heat treatment, the sample is cooled to room temperature. Any access silver remaining on the surface of the substrate can be removed or can be allowed to remain on the surface in the form of "silver islands" on the surface. In one embodiment, at least about 20% of the silver deposited on the surface of the substrate remains on the surface following the diffusing treatment, which percentage is intended to refer to the area fraction of the silver remaining on the surface following diffusion. Area fraction can be calculated using standard stereological methods known in the art. In another embodiment, at least about 60% (area fraction) of the silver deposited on the surface of the substrate remains on the surface following the diffusing treatment. The remainder of the silver is contained in the subsurface zone of the substrate. In another embodiment, after silver diffusion, excess silver on the surface is removed by chemical or mechanical means, examples of which are known to a person skilled in the art.

In another exemplary method, a roughened Zr-2.5Nb substrate having commercially pure silver deposited thereon by PVD is heated to about 685° C. in vacuum, which may be, as an example, less than about $10^{-4}$ torr. The silver-coated substrate is maintained at this temperature for a period of time sufficient for all or nearly all of the silver to become dissolved and diffused into the substrate in the subsurface zone. In one embodiment, the period of time is from about 15 minutes to about 20 hours. In another embodiment, the period of time is from about 30 minutes to about 5 hours. In yet another embodiment, the period of time is from about 15 minutes to about 1 hour. After the heat treatment, the sample is cooled to room temperature. In one embodiment, any excess silver remaining on the surface of the substrate is allowed to remain on the surface in the form of "silver islands" on the surface. In one embodiment, at least about 20% (area fraction) of the silver deposited on the surface of the substrate remains on the surface following the diffusing treatment. In another embodiment, at least about 60% (area fraction) of the silver deposited on the surface of the substrate remains on the surface following the diffusing treatment. The remainder of the silver is contained in the subsurface zone of the substrate. In another embodiment, after silver diffusion, any excess silver remaining on the surface is removed by chemical or mechanical means, examples of which are known to a person skilled in the art.

The composition of the subsurface zone following diffusion can have varying characteristics (referred to herein as "diffusion profiles"), which characteristics can be controlled by varying certain parameters of the process, including, for example, the amount of silver and/or copper deposited on the surface of the substrate, the chemistry of the alloy of the substrate, the surface area of the substrate prior to deposition of silver and/or copper thereon, and the temperature and time during which the diffusion is conducted. In one embodiment, the diffusing produces an exponential diffusion profile of the silver or copper inside the alloy. In another embodiment, the diffusing produces a uniform diffusion profile of the silver or copper inside the alloy. In yet another embodiment, the diffusing produces a sigmoidal shaped diffusion profile. In still another embodiment, the diffusing produces a diffusion profile that is a combination of a step function (which features an abrupt change at the interface between the diffusion zone and the underlying substrate) and an exponential function. Such profiles can be modeled using Fick's laws of diffusion. For example, the diffusion profile (concentration at a distance x in the alloy with time $C(x, t)$) of silver in Ti6Al4V alloy after depositing a thin film of silver on the surface can be modeled using the following equation:

$$C(x, t) = \frac{C_i}{2\sqrt{\pi D^* t}} \exp\left(\frac{-x^2}{4D^* t}\right) \Delta x'$$

where $C_i$ is the concentration of silver deposited on the surface with thickness $\Delta x'$.

Figure 13A:
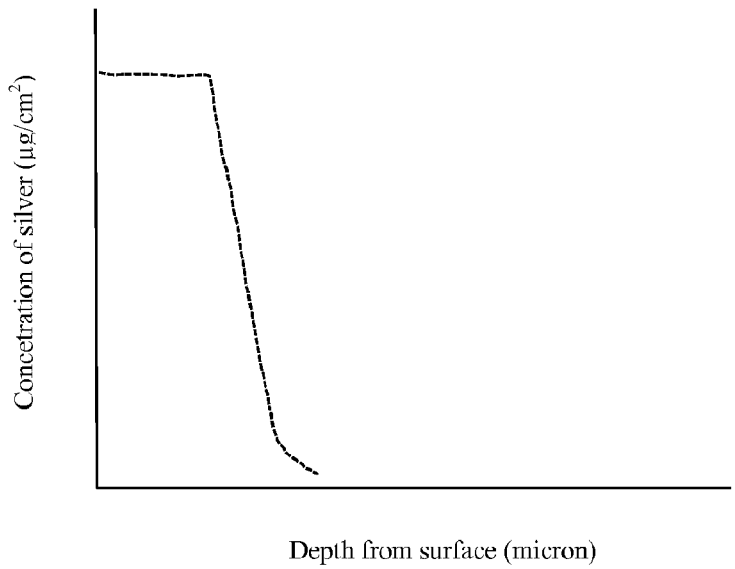
FIGS. 13A-D are schematic representations of four different diffusion profiles as described in the specification.
Figure 13B:
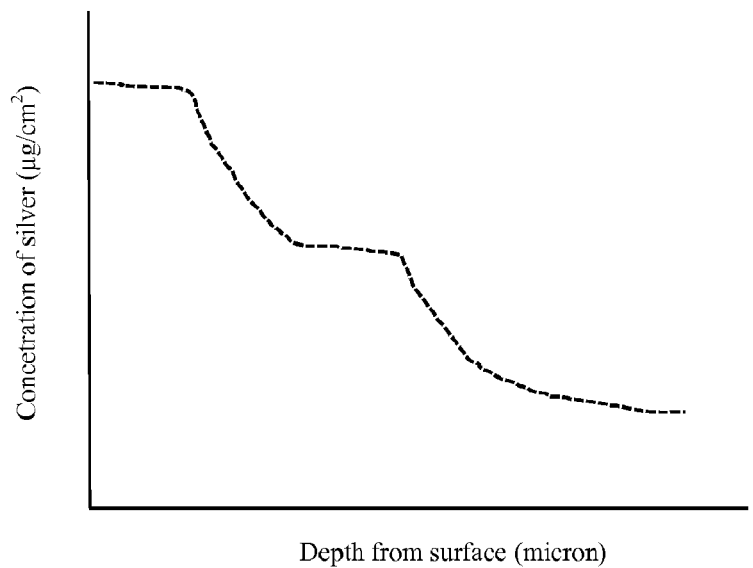
Figure 13C:
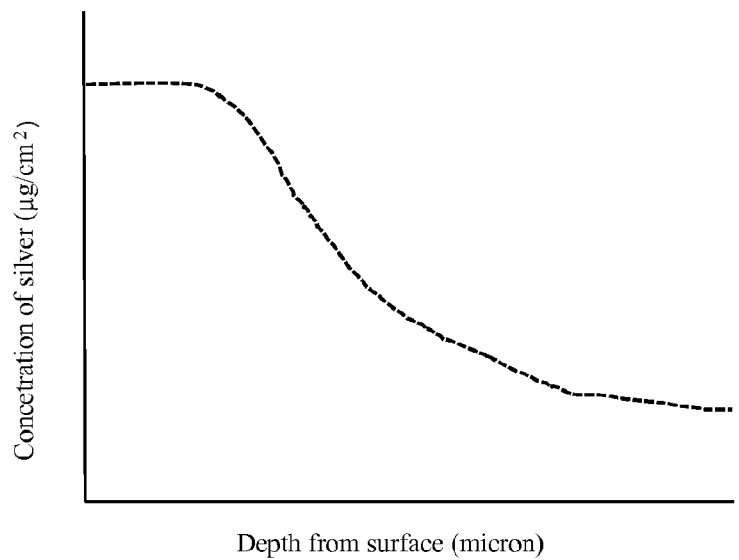
Figure 13D:
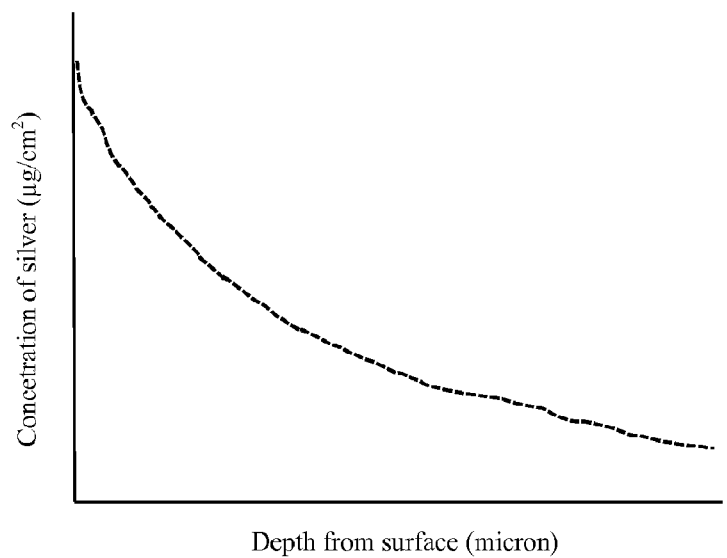

$D^*$ is the diffusion coefficient of silver which is function of temperature and alloy.

t is the of time used for diffusion treatment. Examples of various profiles are shown in FIGS. 13A-D, in which FIG. 13A depicts an example schematic of a step function diffusion profile, FIG. 13B depicts an example schematic of a combination profile, FIG. 13C depicts an example schematic of a sigmoidal profile and FIG. 13D depicts an example schematic of an exponential profile.

The diffusion of silver and/or copper into the substrate can be further enhanced by, after depositing the silver and/or copper onto the surface of the substrate and before the diffusion treatment, wrapping the implant in a silver foil or a copper foil. In one embodiment, an implant having a substrate deposited with silver is wrapped in silver foil to provide an additional source of silver atoms for diffusion. In another embodiment, an implant having a substrate deposited with copper is wrapped in copper foil to provide an additional source of copper atoms for diffusion. In yet another embodiment, an implant having a substrate deposited with silver is wrapped in copper foil to provide a source of copper atoms for diffusion. In still another embodiment, an implant having a substrate deposited with copper is wrapped in silver foil to provide a source of silver atoms for diffusion. In still yet another embodiment, an implant having a substrate deposited with both silver and copper is wrapped in either silver foil or copper foil to provide an additional source of silver or copper atoms for diffusion, respectively. Silver and copper foils can be obtained commercially and can be fully wrapped around the implant or other substrate. In another embodiment, the foil or foils can be placed in proximity with the implant such that heating vaporizes silver atoms, which are then deposited on the surface of the implant at elevated temperatures and under vacuum.

The present disclosure also contemplates that the silver and/or copper foil as discussed above can be used as the sole source of silver atoms and/or copper atoms for diffusion into a metallic substrate. In such an embodiment, the use of silver and/or copper foil operates as a substitute for the above-described deposition of silver and/or copper on a metallic substrate, and can be used in lieu thereof. As such, in another embodiment, the only source of silver is a silver foil wrapped around the implant. In this embodiment the substrate is wrapped in a selected foil, and then exposed to a diffusion treatment as described herein.

After the diffusion is completed as described above to provide a device having a subsurface zone with silver and/or copper integrated therein, the device is exposed to an oxidizing or anodizing treatment. First with regard to an oxidizing treatment, the device can be subjected to oxidization or oxidation at a temperature between about 500 degrees and about 1000 degrees Celsius for 1 hour or more. In one embodiment, the oxidation is carried out at a temperature of from about 500° to about 700° C. for at least one hour. In another embodiment, the oxidation is carried out at a temperature of about 600° C. for about one hour and 15 minutes. The alloy surface after oxidation is illustrated by the cross-sectional image in step 3 of FIG. 1.

In another embodiment, oxidation is achieved by an oxygen ion implantation treatment after the silver and/or copper is diffused in the substrate. The ion implantation can be performed using a vacuum chamber and ionized gas containing oxygen species. The ionization of the gas can be performed using known techniques such as, for example, plasma with electric discharge.

In another embodiment, a device having a subsurface zone with silver and/or copper integrated therein is exposed to an anodizing treatment. In one embodiment, the device is anodized in a bath of ammonium sulfate at a voltage of from about 10 to about 150 V for at least 10 seconds. The ammonium sulfate concentration can range from about 10 g/L to about 60 g/L. In one embodiment the ammonium sulfate has a concentration of from about 30 g/L to about 50 g/L. In one embodiment, the implant can go through a cleaning process before anodization, such as, for example, a cleaning process that comprises cleaning the surface in an alkaline solution, such as, for example, soapy water. The anodization can be performed for a length of time sufficient to produce a desired color and a desired thickness. In one embodiment, the length of time is from about 10 seconds to about 5 minutes.

As will be appreciated from the above descriptions, this document discloses a variety of methods, including, but not limited to, the following embodiments:

(1) A method of incorporating silver, copper or both silver and copper into a metallic biomedical implant that includes: (i) providing an implant comprising a biomedical metal or a biomedical alloy having an outer surface; (ii) depositing silver, copper or both silver and copper onto the outer surface; (iii) diffusing silver, copper or both silver and copper into the biomedical metal or biomedical alloy beneath the outer surface; and (iv) oxidizing or anodizing the outer surface after said diffusing to form an oxidized or anodized layer.

(2) A method in accordance with embodiment 1 that further includes, before said depositing, roughening the outer surface.

(3) A method in accordance with embodiment 2 in which the surface, after said roughening and before said depositing, has a roughness of from about 0.1 micron to about 10 micron Ra.

(4) A method in accordance with any of the above embodiments in which the oxidized or anodized layer contains at least some amount of silver oxide or silver compounds.

(5) A method in accordance with any of the above embodiments that further includes, after said diffusing, removing excess silver or copper on the outer surface by chemical or mechanical means.

(6) A method in accordance with any of the above embodiments that further includes, after said diffusing, exposing the outer surface to an oxygen ion implantation treatment.

(7) A method in accordance with any of the above embodiments that further includes, before said depositing, etching the outer surface using a fluoride solution to remove any native oxide from the outer surface.

(8) A method in accordance with embodiment 7 in which the fluoride solution comprises a solution of hydrofluoric acid and nitric acid or a solution of ammonium fluoride.

(9) A method in accordance with any of the above embodiments in which said diffusing is conducted in vacuum ($<10^{-4}$ Torr) at a temperature between about 700 and about 800° C. for greater than 5 minutes.

(10) A method in accordance with any of the above embodiments in which, after said diffusing, the deposited silver is present in a subsurface zone of the substrate with an exponential or uniform profile.

(11) A method in accordance with any of the above embodiments in which said oxidizing or anodizing comprises a thermal oxidation conducted at a temperature between about 500 and about 1000° C. for at least 1 hour.

(12) A method in accordance with any of the above embodiments in which said diffusing is conducted in an inert atmosphere containing argon or helium or nitrogen.

(13) A method in accordance with any of the above embodiments in which, after said depositing and before said diffusing, the implant is wrapped in silver foil.

(14) A method in accordance with any of the above embodiments in which said depositing comprises wrapping the implant in silver foil.

(15) A method in accordance with any of the above embodiments in which said oxidizing or anodizing comprises anodizing the surface in a bath of ammonium sulfate at a voltage between about 10 and about 150 V for at least 10 seconds.

(16) A method in accordance with any of the above embodiments in which said depositing comprises a member selected from the group consisting of depositing silver using an electrochemical plating process, using a chemical dip process containing silver colloidal solution, using a spraying process or using an ion implantation process.

(17) A method for imparting biofilm resistance to an implant device, the implant device being wholly or partially composed of a metallic substrate, that includes: (i) depositing silver, copper or both silver and copper onto a surface of the metallic substrate; (ii) diffusing the silver, copper or both silver and copper into a subsurface zone of the substrate, the subsurface zone being adjacent the surface and extending to a depth below the surface; and (iii) oxidizing or anodizing the substrate, thereby forming an oxidized or anodized layer at the surface of the substrate.

(18) A method in accordance with any of the above embodiments in which the metallic substrate comprises a biomedical metal or a biomedical alloy.

(19) A method in accordance with any of the above embodiments in which said depositing comprises depositing by physical vapor deposition.

(20) A method in accordance with any of the above embodiments in which, after said depositing, the silver, copper or both silver and copper is present on the substrate in an amount of from about 5 micrograms/cm$^2$ to about 150 micrograms/cm$^2$.

(21) A method in accordance with any of the above embodiments in which said depositing comprises depositing silver onto the surface of the metallic substrate and wherein at least some silver remains on the surface of the substrate following said diffusing.

(22) A method in accordance with any of the above embodiments in which at least about 20 percent (area fraction) of the silver deposited on the surface of the substrate remains on the surface after said diffusing.

(23) A method in accordance with any of the above embodiments in which any excess silver or copper remaining on the surface of the substrate after said diffusing is removed prior to said oxidizing or anodizing.

(24) A method in accordance with any of the above embodiments that further includes, before said depositing, modifying the surface of the substrate to increase the surface area of the substrate.

(25) A method in accordance with embodiment 24 in which said modifying comprises a physical roughening treatment.

(26) A method in accordance with any of the above embodiments in which said modifying comprises a chemical treatment that includes soaking the substrate in an alkaline solution for a period of time of about 1 hour to about 24 hours.

(27) A method in accordance with embodiment 26 in which said soaking is performed at a temperature of from about 30 to about 90° C.

(28) A method in accordance with embodiment 26 in which said alkaline solution comprises sodium hydroxide.

(29) A method in accordance with embodiment 26 that further includes a physical roughening treatment before said chemical treatment.

(30) A method in accordance with any of the above embodiments in which said diffusing comprises heat treating the substrate at a temperature of from about 500° C. to about 800° C., or a temperature of from about 650° C. to about 800° C., for a period of time of about 15 minutes to about 10 hours.

(31) A method in accordance with embodiment 30 in which said heat treating is conducted in air, in a vacuum or in an inert atmosphere containing argon, helium or nitrogen.

(32) A method in accordance with any of the above embodiments in which the oxidized or anodized layer contains at least some amount of silver, copper or both silver and copper.

The term "about" as used herein may be applied to modify any quantitative representation which could permissibly vary without resulting in a change in the basic function to which it is related. For example, heating of a solution as disclosed herein has some flexibility as to temperature that may permissibly vary within several degrees so long as the effect of the treatment is not materially altered.

As various modifications could be made to the exemplary embodiments, as described herein with reference to the corresponding figures, without departing from the scope of the invention, it is intended that all matter contained in this description and shown in the accompanying drawings shall be interpreted as illustrative rather than limiting. The embodiments were chosen and described in order to best explain the principles of the invention and its practical application to thereby enable others skilled in the art to best utilize the invention in various embodiments and with various modifications as are suited to the particular use contemplated. Thus, the breadth and scope of the invention should not be limited by any of the exemplary embodiments described herein, but should be defined only in accordance with the claims and their equivalents.

Reference will now be made to the following Examples, which describe experimental work directed to the subject matter of the present disclosure. It is understood that no limitation to the scope of the invention is intended thereby. The Examples are intended to be illustrative, are provided solely to promote a full understanding of the concepts embodied in the disclosure, and are not intended to be limiting or otherwise restrictive as to the nature and scope of the inventions set forth herein.

EXAMPLES

Example One

Silver was deposited on multiple Ti6Al4V disks using a bench top PVD apparatus (Denton Vacuum LLC, USA) and using a 99.9% pure silver target. The pressure during deposition was approximately 50 mTorr, the current was 30 mA and the deposition was carried out for various times ranging from 1 minute to 5 minutes, thereby controlling the amount of silver that was deposited on the surface of various sample disks. The amount of silver deposited on the disk samples ranged from less than 10 micrograms/cm$^2$ to approximately 140 microgram/cm$^2$.

The samples having silver deposited thereon as described above were then heat treated in a vacuum at 750° C. for 4 hours to diffuse at least a portion of the silver to into the Ti6Al4V substrates. Silver was almost completely diffused in samples with thinner silver deposits; however, samples with thicker silver deposits had islands of silver present thereon following the diffusion treatment.

The samples were then anodized using ammonium sulfate solution with applied voltage ranging from 50 to 70V to produce an anodized surface on the disks.

Figure 3:
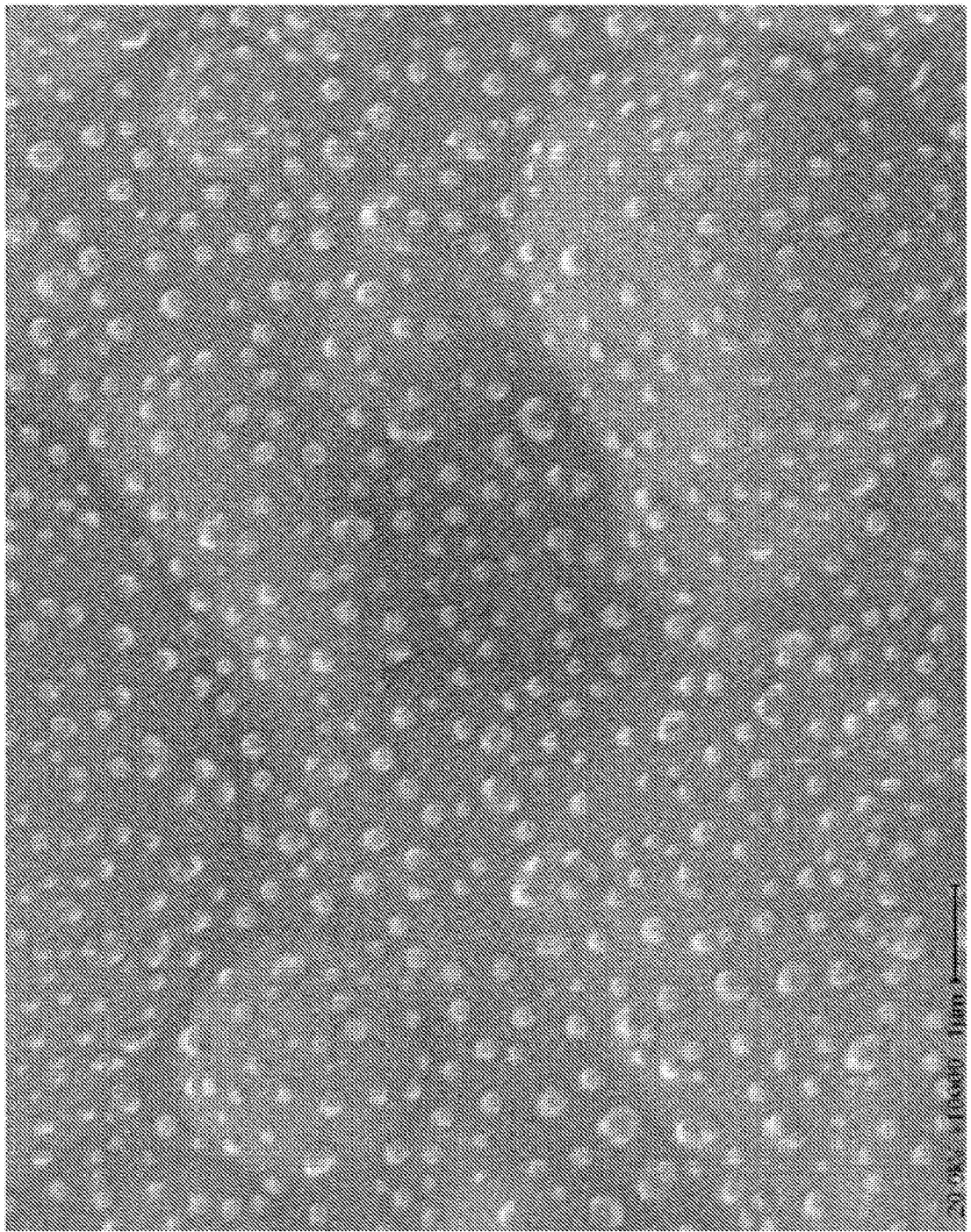
FIG. 3 shows silver deposited on Ti6Al4V surface (as-sputtered) as described in Example One.

FIG. 3 shows silver deposited on the surface of one of the Ti6Al4V samples (as-sputtered, i.e., prior to diffusion treatment). The image is taken in secondary electron mode to appearance of as-sputtered surface. The surface is characterized by nanometer-sized deposits and some large globules.

Figure 4:
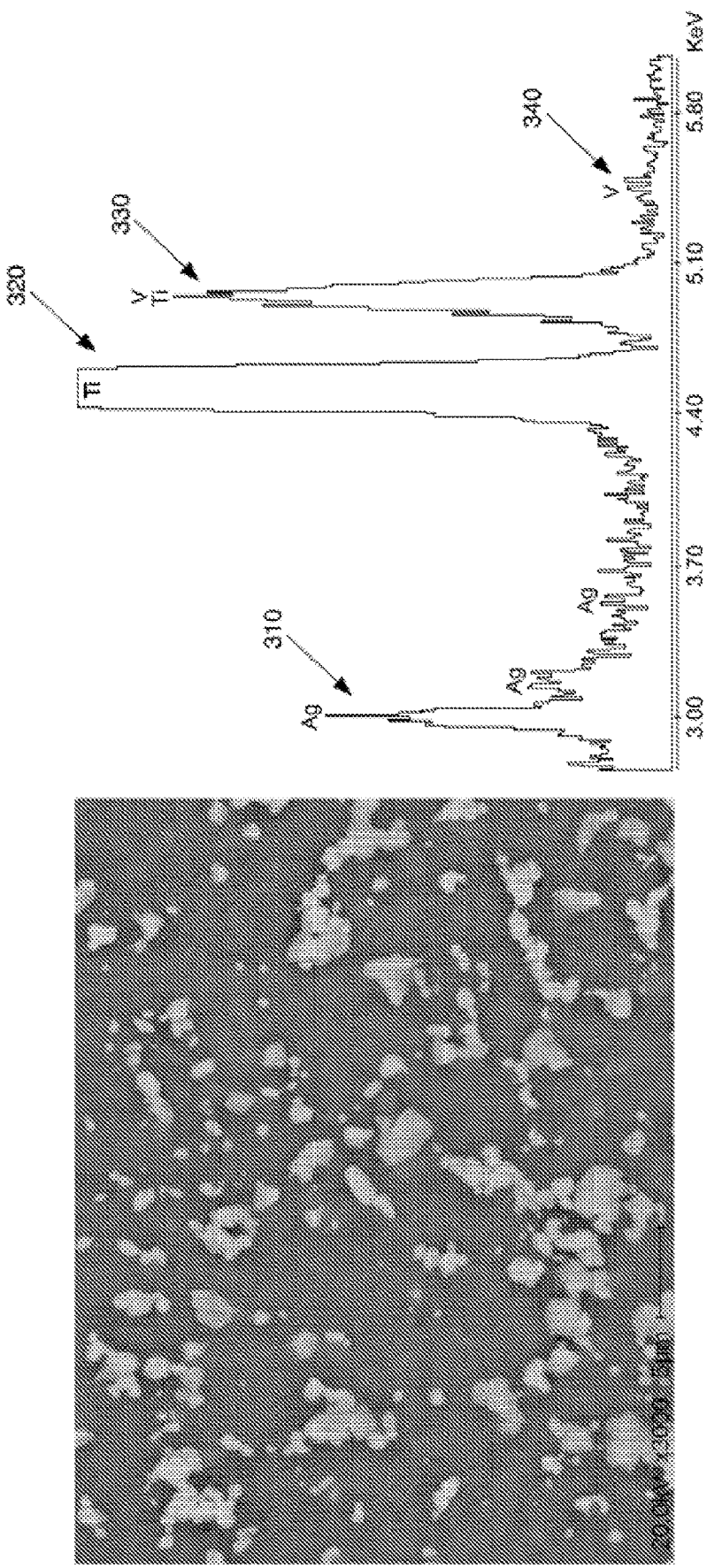
FIG. 4 shows a sample with silver islands still remaining on the surface after heat treatment as described in Example One.
Figure 5:
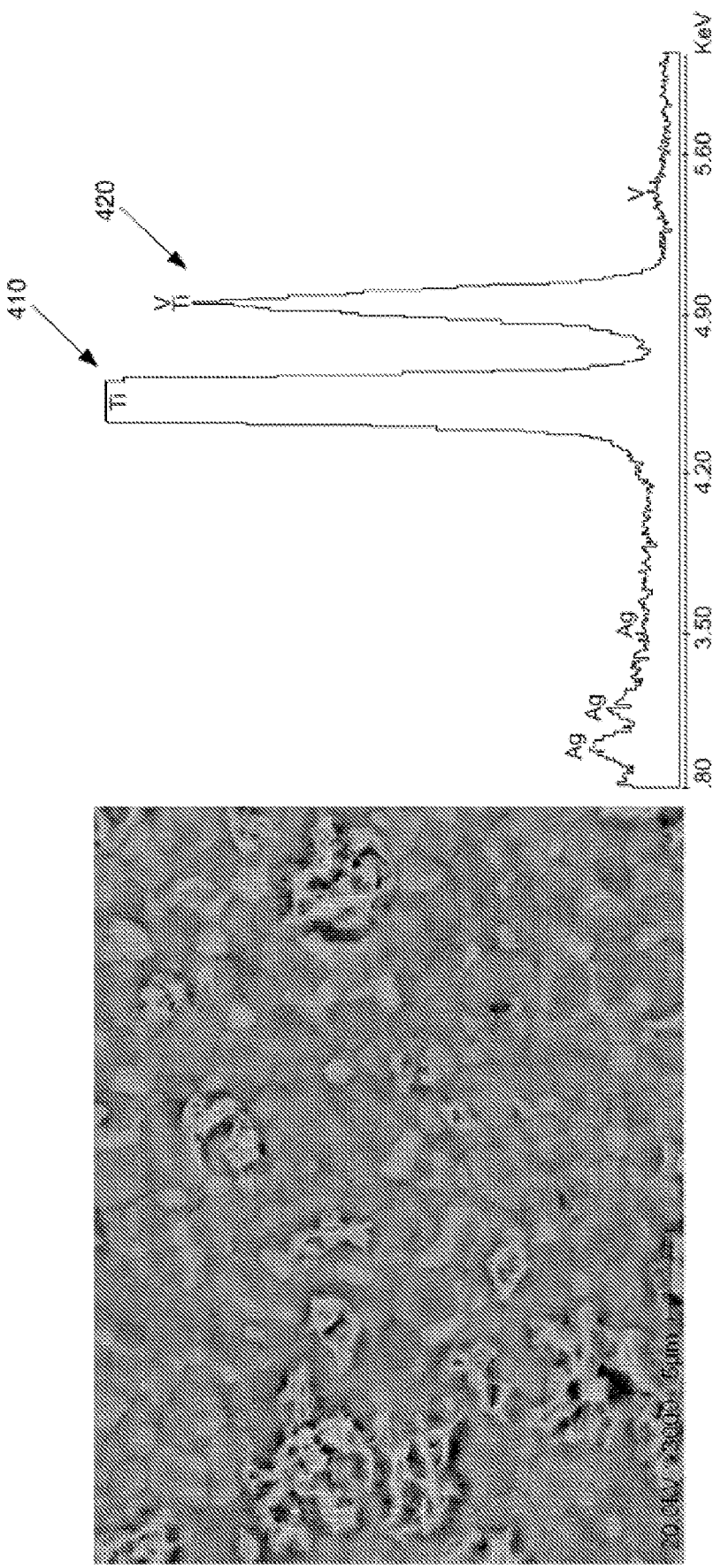
FIG. 5 shows a sample with no discernible "silver islands" after heat treatment, indicating that most of the silver has been alloyed or diffused in the substrate as described in Example One.

FIGS. 4 and 5 are SEM images of two samples following diffusion treatment as described above, taken in back-scattered electron mode to contrast silver 310 (higher atomic number) with the Ti6Al4V substrate 320, 330 (lower atomic number). The sample depicted in FIG. 4 is one upon which a relatively thicker layer of silver was originally deposited, and the SEM shows silver islands still remaining on the surface after diffusion treatment at 750° Celsius for about four hours in vacuum. Silver peak 310 can be seen in the energy dispersive spectra. The sample depicted in FIG. 5 is one upon which a relatively thinner layer of silver was originally deposited, and has no discernible "silver islands" after diffusion treatment 750° Celsius for about four hours in vacuum, indicating that most of the deposited silver has been alloyed or diffused in the substrate. In FIG. 5, the grain boundaries of the substrate and some localized etching of the substrate seem to have occurred. Silver signal is visible in the energy dispersive spectra. The peak is smaller than that observed in FIG. 4, thus indicating lower concentration of silver on the surface.

Figure 6:
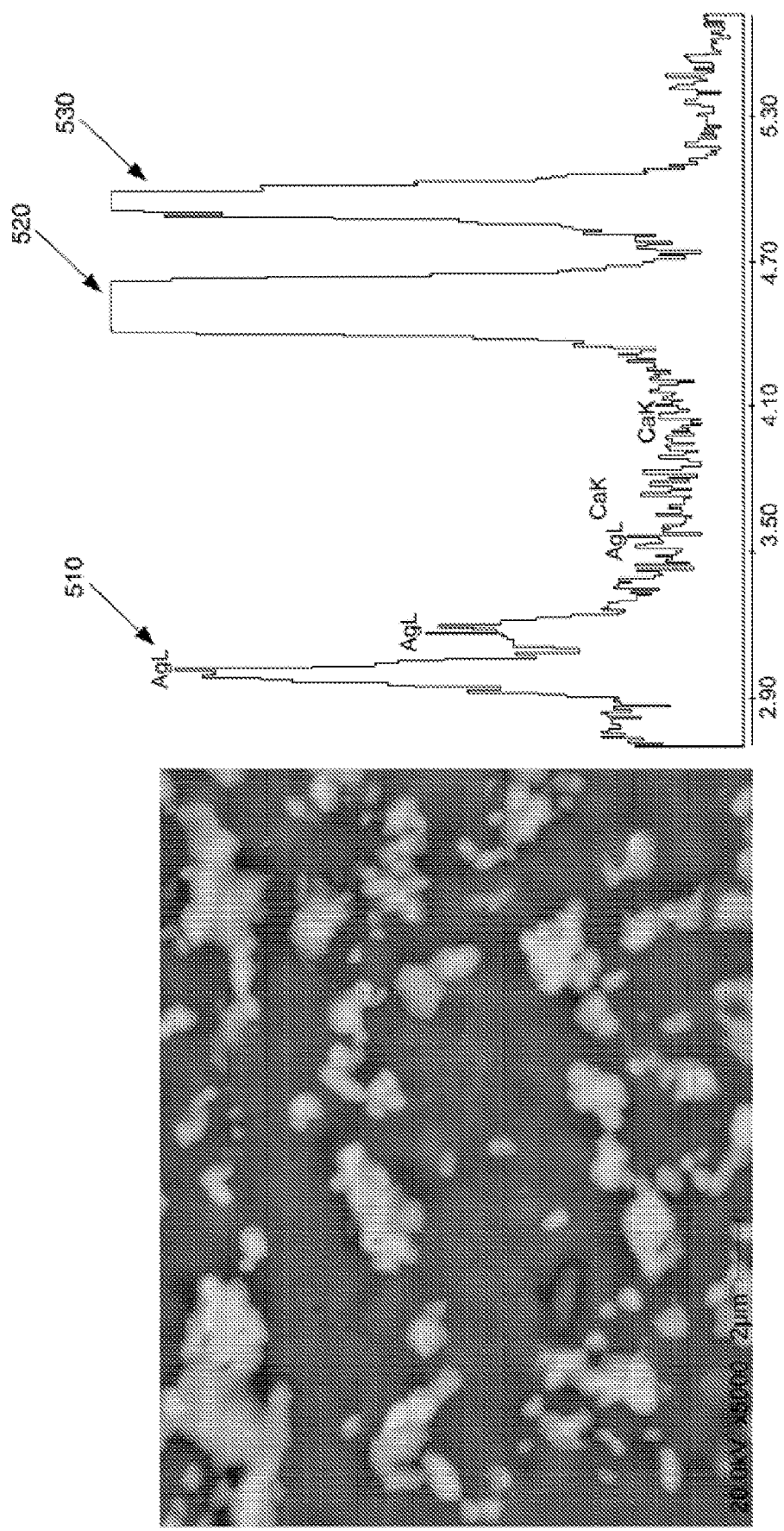
FIG. 6 shows a back-scattered electron image of the anodized surface of a sample with silver islands intact on the surface as described in Example One.
Figure 7:
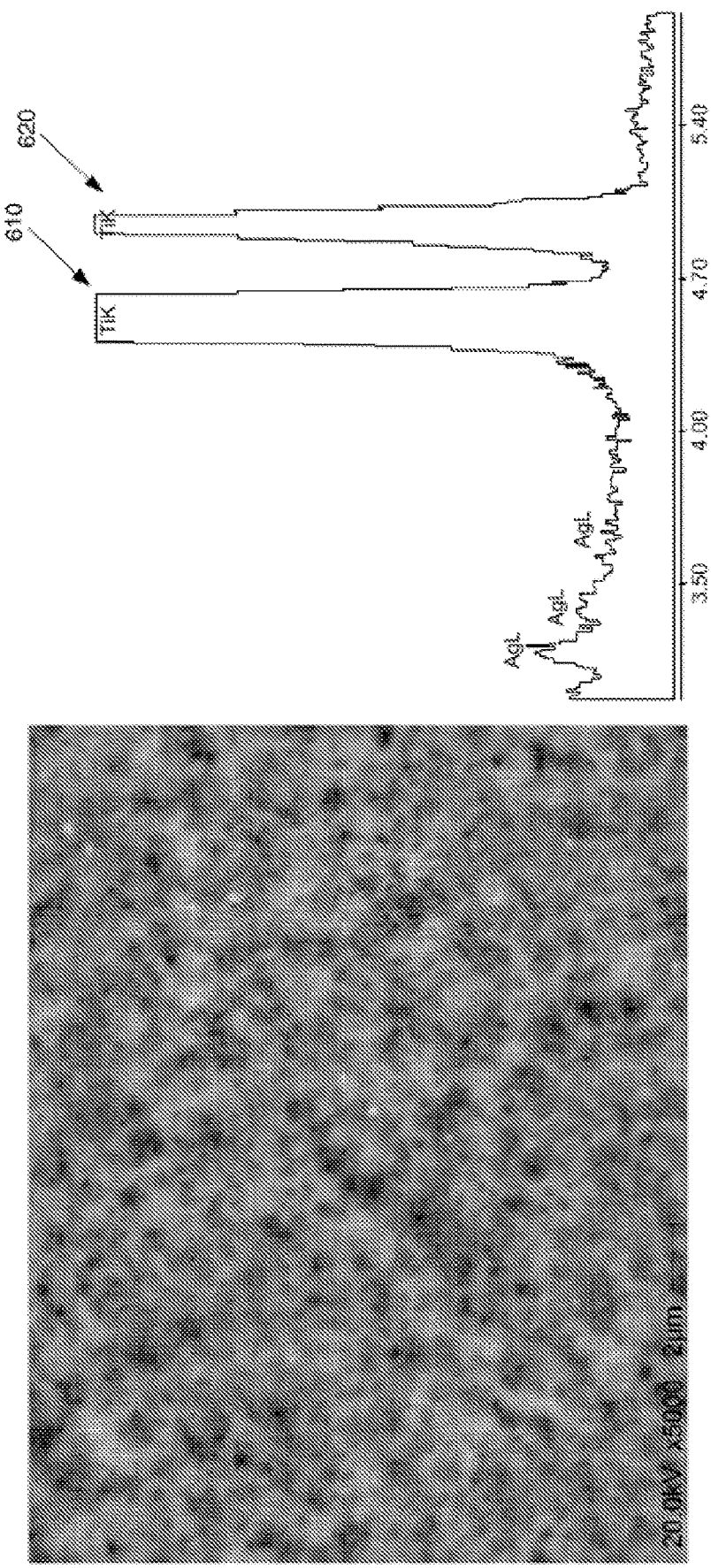
FIG. 7 shows a back-scattered electron image of the anodized surface of a sample with most of the silver diffused in the Ti6Al4V alloy as described in Example One.

FIGS. 6 and 7 depict back-scattered electron images of the samples depicted in FIGS. 4 and 5, but after anodizing treatment. FIG. 6 depicts the anodized surface of the sample with silver islands intact on the surface, and FIG. 7 depicts the anodized surface of the sample with most of the silver diffused in Ti6Al4V alloy. Few small particulates of silver 630 (brighter in appearance) are visible in the image.

Example Two

A Ti6Al4V disk having a diameter of 1 inch and a thickness of ¼ inch was grit blasted to increase the surface area of the disk. Silver was then deposited on the surface of the disk using PVD as described in Example One, with deposition conditions set as follows: pressure during deposition was 48 mTorr, the current set point was 33 mA and the deposition was carried out for 300 seconds. The disk with silver deposited thereon as described above was then heat treated in a vacuum (<10$^{-5}$ Torr) at 750° C. for 15 minutes to diffuse at least a portion of the silver to into the Ti6Al4V substrate. The disk was then anodized using ammonium sulfate solution at 64V for 45 seconds to produce an anodized surface on the disk.

Figure 10A:
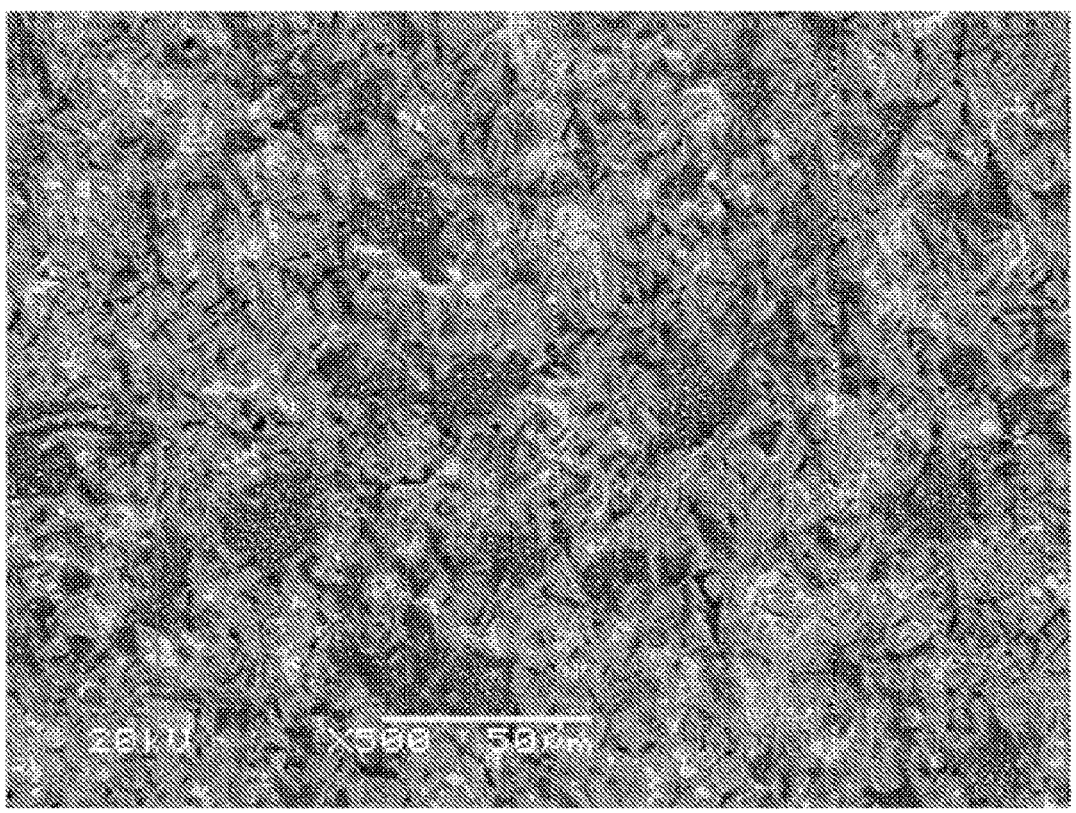
FIGS. 10A-C are scanning electron micrographs of surface portions of a disk made as described in Example Two.
Figure 10B:
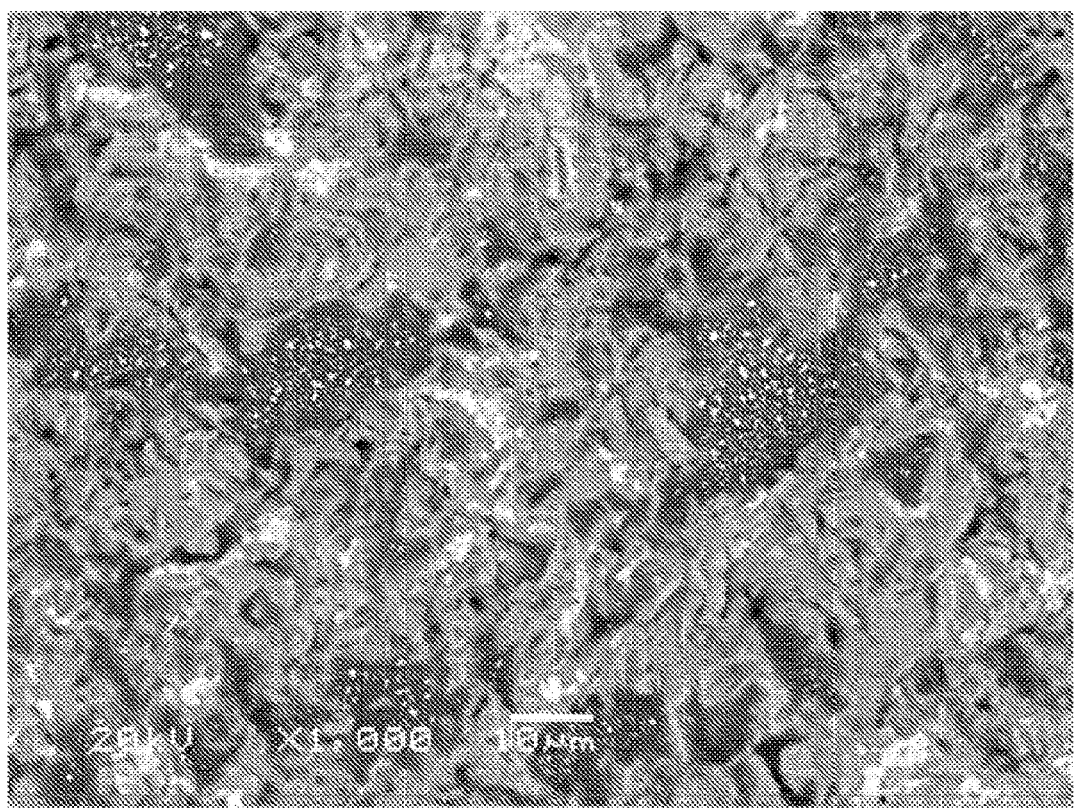
Figure 10C:
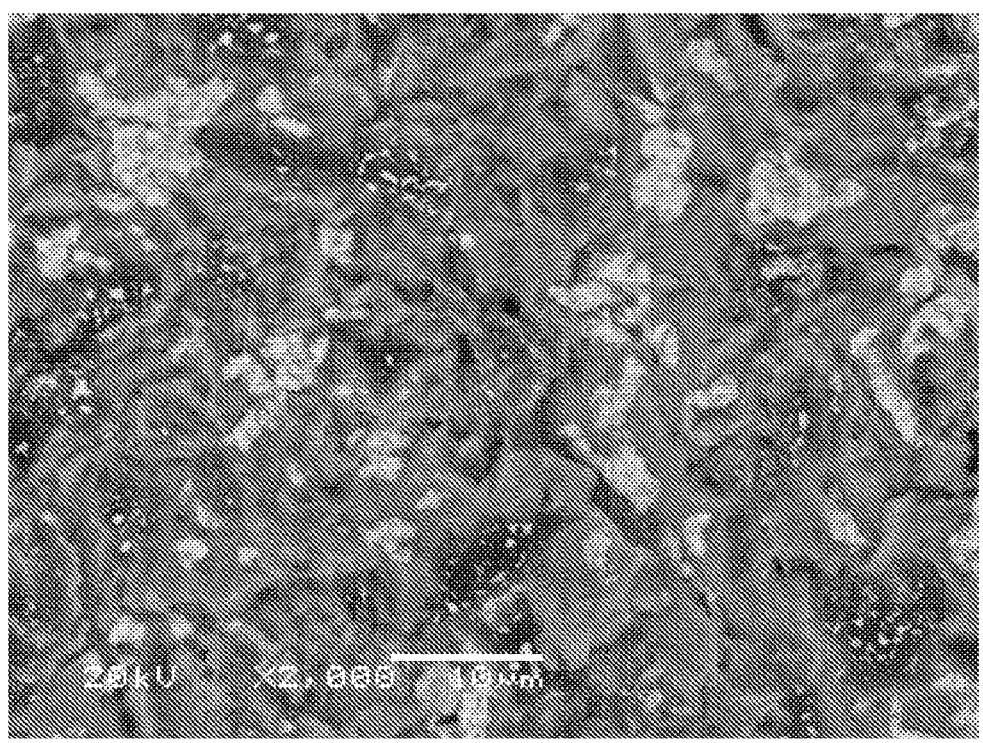

FIGS. 10A-C are scanning electron micrographs (SEMs) of surface portions of the disk made as described above, with .times.500 magnification (FIG. 10A), .times.1,000 magnification (FIG. 10B) and .times.2,000 magnification (FIG. 10C). FIGS. 10A-C show silver deposited on the surface of the disk. The image is taken in secondary electron mode. The surface is characterized by nanometer-sized deposits and some large globules.

Example Three

A Zr-2.5Nb disk was roughened with 2400 grit paper to increase the surface area of the disk. Silver was then deposited on the surface of the disk using PVD as described in Example One, with deposition conditions set as follows: pressure during deposition was 48 mTorr, the current set point was 33 mA and the deposition was carried out for 300 seconds. The disk with silver deposited thereon as described above was then heat treated in a vacuum ($<10^{-4}$ Torr) at 685° C. for 15 minutes to diffuse at least a portion of the silver to into the Zr-2.5Nb substrate. The disk was then oxidized at 600° C. for 75 minutes.

Figure 11A:
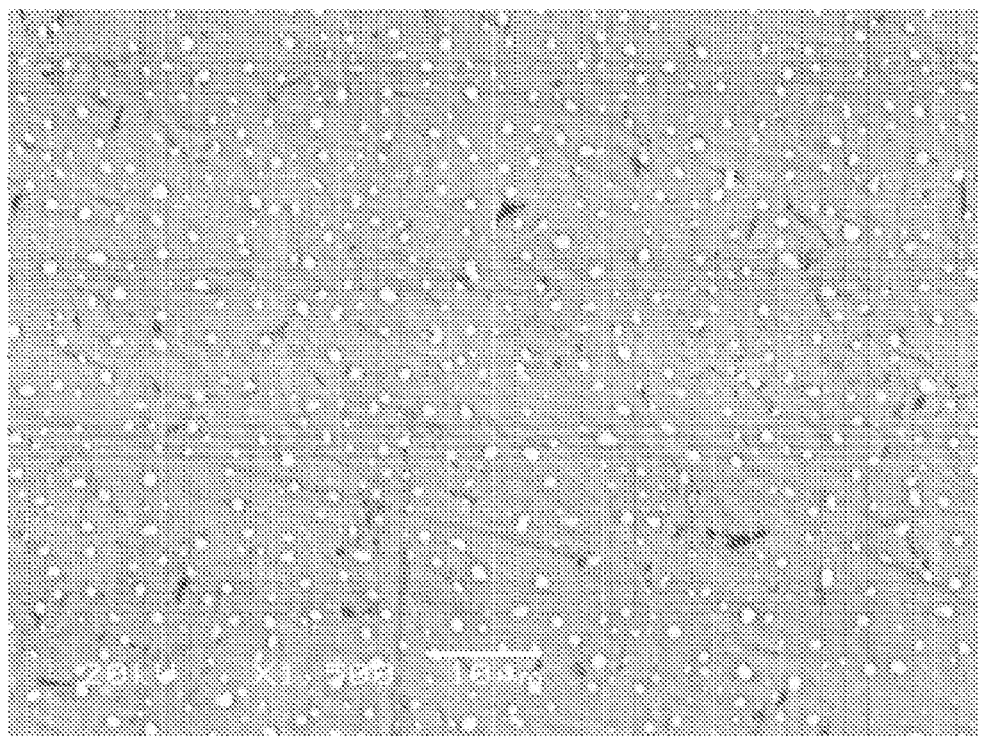
FIGS. 11A-C are scanning electron micrographs of surface portions of a disk made as described in Example Three.
Figure 11B:
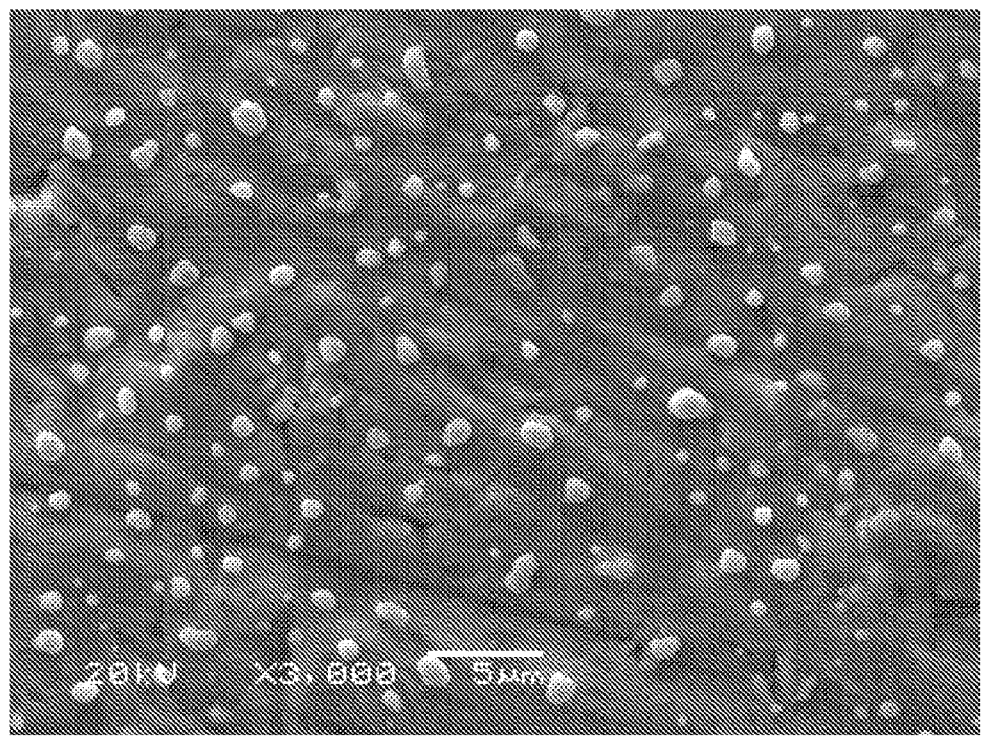
Figure 11C:
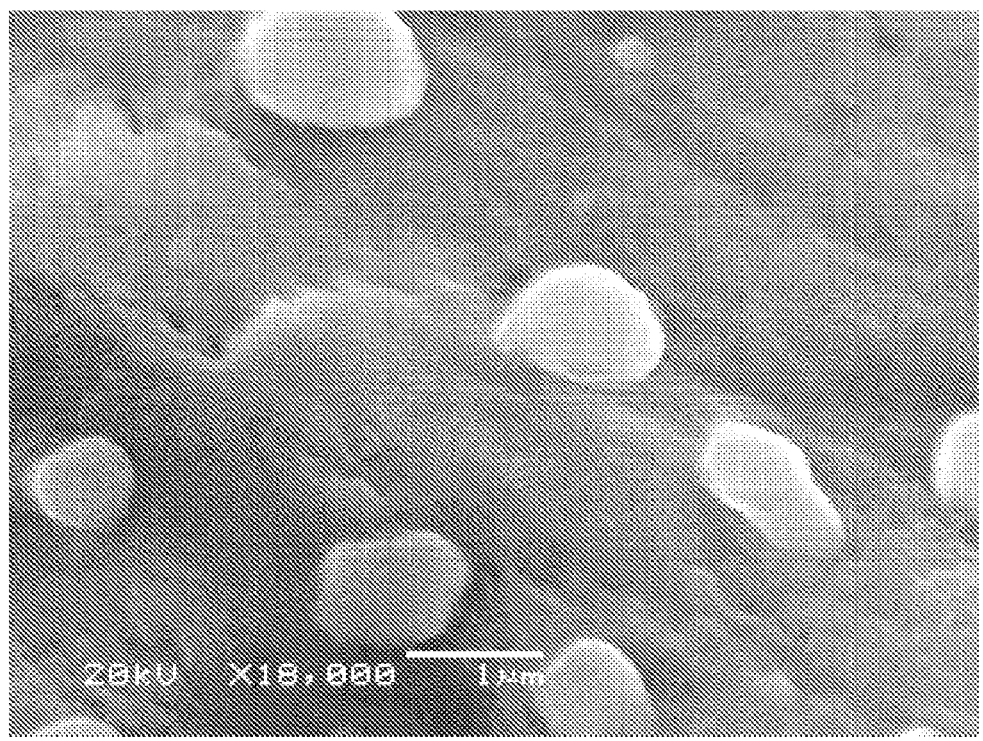

FIGS. 11A-C are SEMs of surface portions of the disk made as described above, with .times.1.500 magnification (FIG. 11A), .times.3,000 magnification (FIG. 11B) and .times.18,000 magnification (FIG. 11C). FIGS. 11A-C show silver deposited on the surface of the disk. The image is taken in secondary electron mode. The surface is characterized by nanometer-sized silver deposits and some large globules.

Example Four

Figure 12A:
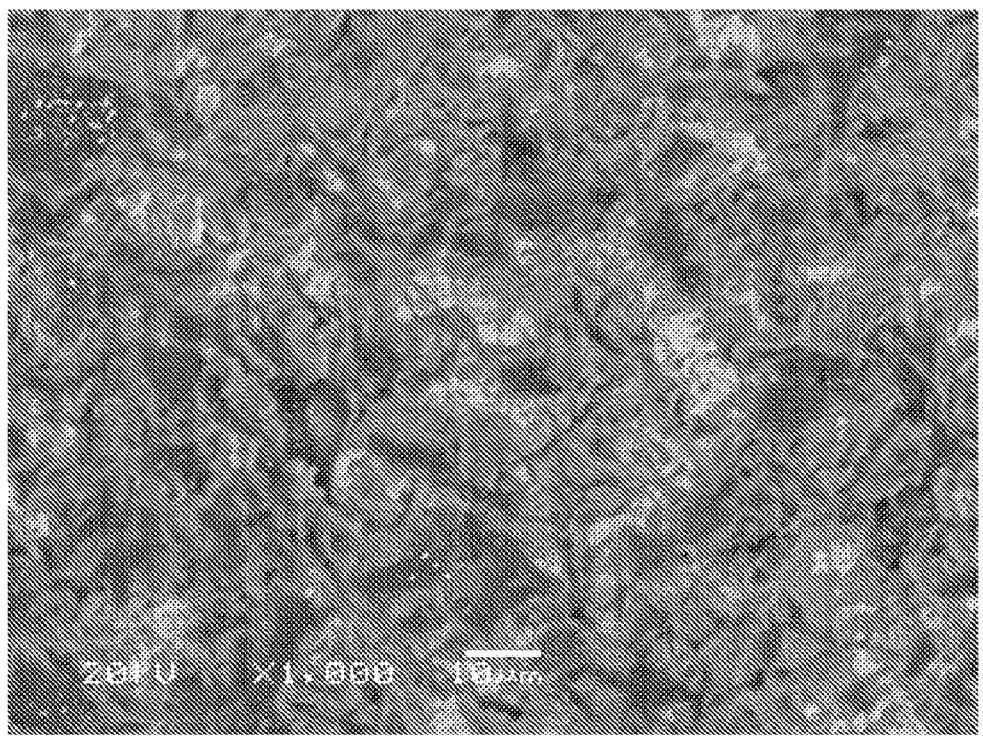
FIGS. 12A-B are scanning electron micrographs of surface portions of a disk made as described in Example Two after soaking in Ringer's solution for 24 hours as described in Example Four.
Figure 12B:
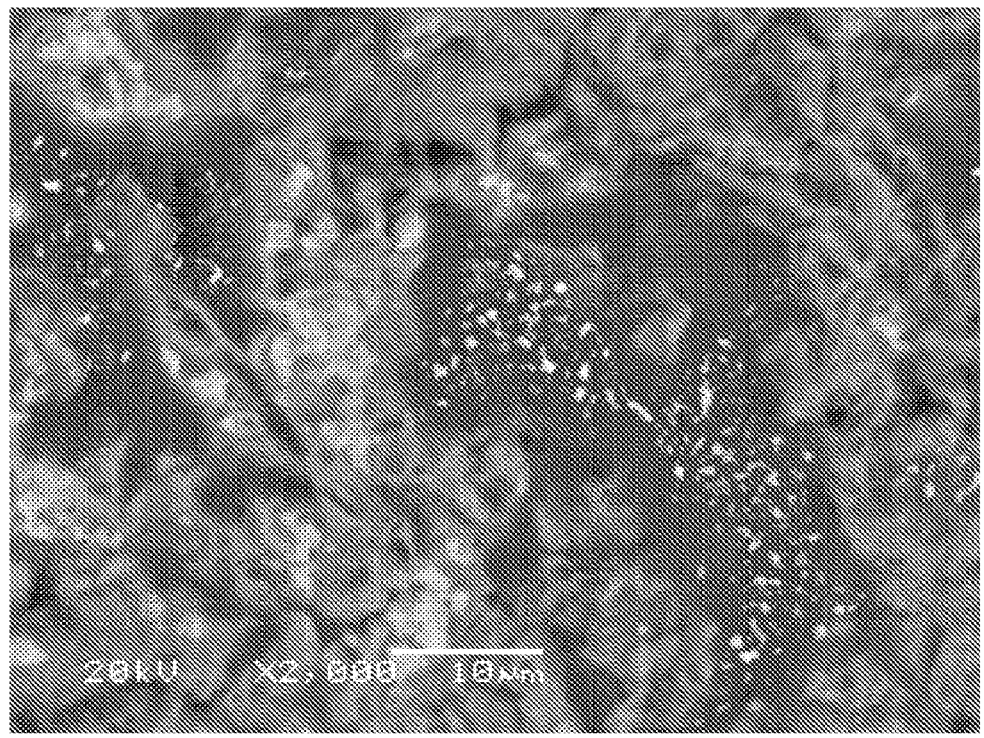

A disk prepared as described in Example Two was immersed in Ringer's solution. After 24 hours, a small aliquot of the solution was drawn from the bath and analyzed to determine the release rate of silver in the first 24 hours. The appearance of the disk surface after 24 hours in Ringer's solution is shown in FIGS. 12A and 12B, which are SEMs of the disk surface at .times.1,000 magnification (FIG. 12A) and .times.2,000 magnification (FIG. 12B). FIGS. 12A and 12B show the presence of silver islands on the surface.

On Day 13, the bath was completely replaced with fresh Ringer's solution. After 24 hours following placement of the disk in fresh Ringer's solution (i.e., on Day 14), a small aliquot was drawn from the bath and analyzed to determine the release rate of silver at Day 14. The results are set forth below in Table 1:

| Day | Release rate in µg/cm$^2$ |
|---|---|
| 1 | 0.3 |
| 14 | 0.007 |

The invention claimed is:

1. A method of incorporating silver, copper or both silver and copper into a metallic biomedical implant, comprising:
   providing an implant comprising a biomedical metal or a biomedical alloy having an outer surface;
   roughening the outer surface of the implant;
   after roughening the outer surface of the implant, depositing silver, copper or both silver and copper onto the outer surface;
   diffusing silver, copper or both silver and copper into the biomedical metal or biomedical alloy beneath the outer surface by heating the implant; and
   oxidizing or anodizing the outer surface after said diffusing to form an oxidized or anodized layer.

2. The method of claim 1, wherein the oxidized or anodized layer contains at least some amount of elemental silver, silver oxide or silver compounds.

3. The method of claim 1, wherein the surface, after said roughening and before said depositing, has a roughness of from about 0.1 micron to about 10 micron Ra.

4. The method of claim 1 wherein said roughening comprises a physical roughening treatment, a chemical treatment that includes soaking the substrate in an alkaline solution for a period of time of about 1 hour to about 24 hours, or both the physical roughening and the chemical treatment.

5. The method of claim 1, wherein said diffusing is conducted in vacuum at a temperature between about 700 and about 800° C. for greater than 5 minutes.

6. The method of claim 1, wherein said diffusing is conducted in an inert atmosphere containing argon or helium or nitrogen.

7. The method of claim 1, wherein said diffusing is conducted in an inert atmosphere.

8. The method of claim 1, wherein said diffusing is conducted in a vacuum.

9. A method of incorporating silver, copper or both silver and copper into a metallic biomedical implant, comprising:
   providing an implant comprising a biomedical metal or a biomedical alloy having an outer surface;
   etching the outer surface using a fluoride solution;
   after etching the outer surface, depositing silver, copper or both silver and copper onto the outer surface;
   diffusing silver, copper or both silver and copper into the biomedical metal or biomedical alloy beneath the outer surface by heating the implant; and
   oxidizing or anodizing the outer surface after said diffusing to form an oxidized or anodized layer.

10. A method of incorporating silver, copper or both silver and copper into a metallic biomedical implant, comprising:
    providing an implant comprising a biomedical metal or a biomedical alloy having an outer surface;
    depositing silver, copper or both silver and copper onto the outer surface;
    diffusing silver, copper or both silver and copper into the biomedical metal or biomedical alloy beneath the outer surface by heating the implant; and
    oxidizing or anodizing the outer surface after said diffusing to form an oxidized or anodized layer;
    wherein at least about 20 percent, by area fraction, of the silver deposited on the surface of the substrate remains on the surface after said diffusing.

11. A method of incorporating silver, copper or both silver and copper into a metallic biomedical implant, comprising:
    providing an implant comprising a biomedical metal or a biomedical alloy having an outer surface;
    depositing silver, copper or both silver and copper onto the outer surface;
    diffusing silver, copper or both silver and copper into the biomedical metal or biomedical alloy beneath the outer surface by heating the implant;
    after said diffusing, removing excess silver or copper on the outer surface by chemical or mechanical means; and
    oxidizing or anodizing the outer surface after said diffusing to form an oxidized or anodized layer.

12. A method of incorporating silver, copper or both silver and copper into a metallic biomedical implant, comprising:
    providing an implant comprising a biomedical metal or a biomedical alloy having an outer surface;
    depositing silver, copper or both silver and copper onto the outer surface;

diffusing silver, copper or both silver and copper into the biomedical metal or biomedical alloy beneath the outer surface by heating the implant;

after said diffusing, exposing the outer surface to an oxygen ion implantation treatment; and oxidizing or anodizing the outer surface after said diffusing to form an oxidized or anodized layer.

13. A method of incorporating silver, copper or both silver and copper into a metallic biomedical implant, comprising:

providing an implant comprising a biomedical metal or a biomedical alloy having an outer surface;

depositing silver, copper or both silver and copper onto the outer surface;

diffusing silver, copper or both silver and copper into the biomedical metal or biomedical alloy beneath the outer surface by heating the implant; and oxidizing or anodizing the outer surface after said diffusing to form an oxidized or anodized layer;

wherein said oxidizing or anodizing comprises a thermal oxidation conducted at a temperature between about 500 and about 1000° C. for at least 1 hour.

14. A method of incorporating silver, copper or both silver and copper into a metallic biomedical implant, comprising:

providing an implant comprising a biomedical metal or a biomedical alloy having an outer surface;

depositing silver, copper or both silver and copper onto the outer surface;

diffusing silver, copper or both silver and copper into the biomedical metal or biomedical alloy beneath the outer surface by heating the implant; and oxidizing or anodizing the outer surface after said diffusing to form an oxidized or anodized layer;

wherein said oxidizing or anodizing comprises anodizing the surface in a bath of ammonium sulfate at a voltage between about 10 and about 150 V for at least 10 seconds.

15. A method of incorporating silver, copper or both silver and copper into a metallic biomedical implant, comprising, providing an implant comprising a biomedical metal or a biomedical alloy having an outer surface;

depositing silver, copper or both silver and copper onto the outer surface;

after said depositing wrapping the implant in silver foil;

after wrapping the implant in silver foil, diffusing silver, copper or both silver and copper into the biomedical metal or biomedical alloy beneath the outer surface by heating the implant; and oxidizing or anodizing the outer surface after said diffusing to form an oxidized or anodized layer.

16. A method of incorporating silver, copper or both silver and copper into a metallic biomedical implant, comprising:

providing an implant comprising a biomedical metal or a biomedical alloy having an outer surface;

depositing silver, copper or both silver and copper onto the outer surface;

diffusing silver, copper or both silver and copper into the biomedical metal or biomedical alloy beneath the outer surface by heating the implant; and oxidizing or anodizing the outer surface after said diffusing to form an oxidized or anodized layer;

wherein said depositing comprises wrapping the implant in silver foil.

17. A method of incorporating silver, copper or both silver and copper into a metallic biomedical implant, comprising:

providing an implant comprising a biomedical metal or a biomedical alloy having an outer surface;

depositing silver, copper or both silver and copper onto the outer surface;

diffusing silver, copper or both silver and copper into the biomedical metal or biomedical alloy beneath the outer surface by heating the implant; and oxidizing or anodizing the outer surface after said diffusing to form an oxidized or anodized layer;

wherein said diffusing is conducted in air.

18. A method of incorporating silver, copper or both silver and copper into a metallic biomedical implant, comprising:

providing an implant comprising a biomedical metal or a biomedical alloy having an outer surface;

depositing silver, copper or both silver and copper onto the outer surface;

diffusing silver, copper or both silver and copper into the biomedical metal or biomedical alloy beneath the outer surface by heating the implant; and oxidizing or anodizing the outer surface after said diffusing to form an oxidized or anodized layer;

wherein said diffusing comprises heating at a temperature of from about 500° C. to about 800° C.

19. A method of incorporating silver, copper or both silver and copper into a metallic biomedical implant, comprising:

providing an implant comprising a biomedical metal or a biomedical alloy having an outer surface;

depositing silver, copper or both silver and copper onto the outer surface;

diffusing silver, copper or both silver and copper into the biomedical metal or biomedical alloy beneath the outer surface by heating the implant; and oxidizing or anodizing the outer surface after said diffusing to form an oxidized or anodized layer;

wherein said diffusing comprises heating at a temperature of from about 650° C. to about 800° C. for a period of time of about 15 minutes to about 10 hours.

* * * * *